(12) United States Patent
Dundon et al.

(10) Patent No.: US 11,691,817 B2
(45) Date of Patent: *Jul. 4, 2023

(54) YEAST CELLS HAVING DISRUPTED PATHWAY FROM DIHYDROXYACETONE PHOSPHATE TO GLYCEROL

(71) Applicant: CARGILL, INCORPORATED, Wayzata, MN (US)

(72) Inventors: Catherine Asleson Dundon, Minneapolis, MN (US); Pirkko Suominen, Maple Grove, MN (US); Aristos Aristidou, Excelsior, MN (US); Brian J. Rush, Minneapolis, MN (US); Kari Koivuranta, Helsinki (FI); Benjamin Matthew Hause, Currie, MN (US); Thomas William McMullin, Minnetonka, MN (US); Kevin Roberg-Perez, Minneapolis, MN (US)

(73) Assignee: CARGILL, INCORPORATED, Wayzata, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/154,190

(22) Filed: Jan. 21, 2021

(65) Prior Publication Data

US 2021/0155411 A1    May 27, 2021

Related U.S. Application Data

(60) Continuation of application No. 15/941,274, filed on Mar. 30, 2018, now Pat. No. 10,899,544, which is a continuation of application No. 14/720,899, filed on May 25, 2015, now abandoned, which is a division of application No. 12/281,286, filed as application No. PCT/US2007/006408 on Mar. 13, 2007, now abandoned.

(60) Provisional application No. 60/781,674, filed on Mar. 13, 2006.

(51) Int. Cl.

| | | |
|---|---|---|
| C12N 15/52 | (2006.01) | |
| B65G 15/12 | (2006.01) | |
| C12P 7/06 | (2006.01) | |
| C12P 7/40 | (2006.01) | |
| C12P 7/56 | (2006.01) | |
| B65G 17/12 | (2006.01) | |
| E01B 29/32 | (2006.01) | |

(52) U.S. Cl.
CPC ............ B65G 15/12 (2013.01); B65G 17/12 (2013.01); C12N 15/52 (2013.01); C12P 7/06 (2013.01); C12P 7/40 (2013.01); C12P 7/56 (2013.01); E01B 29/32 (2013.01); Y02E 50/10 (2013.01); Y10T 137/85986 (2015.04)

(58) Field of Classification Search
CPC .... C12N 15/52; C12P 7/06; C12P 7/40; C12P 7/56; Y02E 50/10
See application file for complete search history.

(56) References Cited

U.S. PATENT DOCUMENTS

| | | |
|---|---|---|
| 4,275,234 A | 6/1981 | Baniel |
| 4,771,001 A | 9/1988 | Bailey |
| 5,132,456 A | 7/1992 | King |
| 5,420,304 A | 5/1995 | Verser |
| 5,510,526 A | 4/1996 | Baniel |
| 5,641,406 A | 6/1997 | Sarhaddar |
| 5,831,122 A | 11/1998 | Eyal |
| 6,268,189 B1 | 7/2001 | Skory |
| 6,329,183 B1 | 12/2001 | Skraly |
| 6,485,947 B1 | 11/2002 | Rajgarhia |
| 8,455,239 B2 | 6/2013 | Feldman |
| 9,777,280 B2 | 10/2017 | Jessen |
| 10,260,072 B2 | 4/2019 | Jessen |
| 10,633,664 B2 | 4/2020 | Jessen |
| 2003/0228671 A1 | 12/2003 | Hause |
| 2004/0029256 A1 | 2/2004 | Rajgarhia |
| 2007/0161098 A1 | 7/2007 | Yamaguchi |
| 2009/0104675 A1 | 4/2009 | Yamaguchi |

FOREIGN PATENT DOCUMENTS

| | | |
|---|---|---|
| EP | 0557365 B1 | 9/1996 |
| JP | 2004521619 A | 7/2004 |
| JP | 2004265655 A | 9/2004 |
| JP | 2006075133 A | 3/2006 |
| WO | 1993000440 A1 | 1/1993 |
| WO | 9914335 W | 3/1999 |
| WO | 1999028480 A1 | 6/1999 |
| WO | 0071738 W | 11/2000 |
| WO | 0242471 W | 5/2002 |
| WO | 2003049525 A2 | 6/2003 |

(Continued)

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Branden et al., Introduction to Protein Structure, Garland Publishing Inc., New York, p. 247, 1991.*
Nguyen et al., Metabolic Engineering 6:155-163, 2004.*

(Continued)

*Primary Examiner* — Delia M Ramirez

(57) ABSTRACT

Yeast cells are genetically modified to disrupt a native metabolic pathway from dihydroxyacetone to glycerol. In certain aspects, the yeast cell is of the genera *Kluyveromyces, Candida* or *Issatchenkia*. In other aspects, the yeast cell is capable of producing at least one organic acid, such as lactate. The yeast cells produce significantly less glycerol than the wild-type strains, and usually produce greater yields of desired fermentation products. Yeast cells of the invention often grow well when cultivated, despite their curtailed glycerol production.

6 Claims, 14 Drawing Sheets

Figure 1:
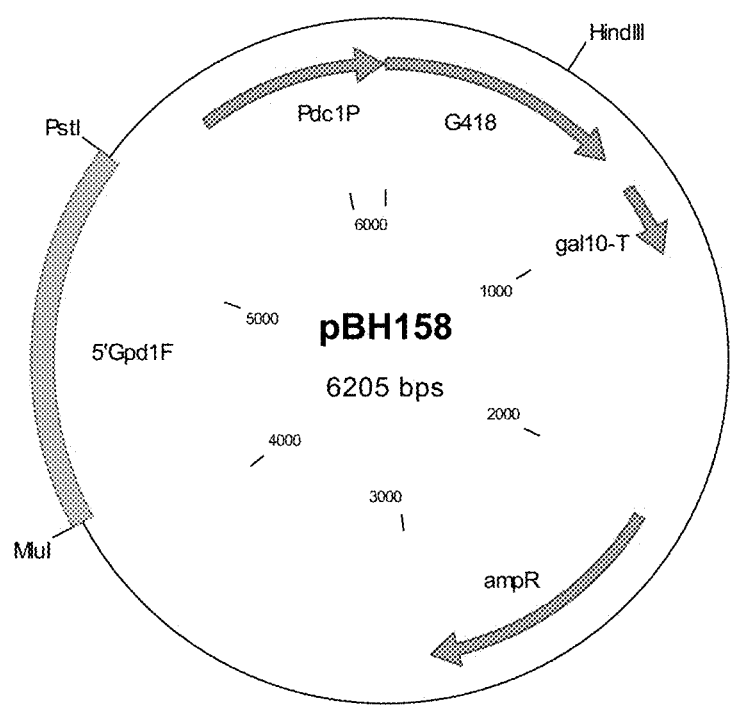

Specification includes a Sequence Listing.

(56) References Cited

FOREIGN PATENT DOCUMENTS

| WO | 2003102152 A2 | | 12/2003 |
|---|---|---|---|
| WO | 2003102200 A2 | | 12/2003 |
| WO | 2003102201 A2 | | 12/2003 |
| WO | WO 2004/048559 | * | 6/2004 |
| WO | 2004099381 A2 | | 11/2004 |
| WO | 2005118719 A2 | | 12/2005 |
| WO | 2006030799 A1 | | 3/2006 |

OTHER PUBLICATIONS

Ishida et al., Applied and Environmental Microbiology 71(4):1964-1970, 2005.*
Valadi et al., Applied Microbiology and Biotechnology 50:434-439, 1998.*
Albertyn, Molecular and Cellular Biology, vol. 14, No. 6, Jun. 1994, p. 4135-4144.
Ansell, The EMBO Journal, vol. 16, No. 9, pp. 2179-2187, 1997.
Appl. Environ. Microbiol., vol. 68, No. 6, p. 2814-2821 (2002).
Bro et al., "In silico aided metabolic engineering of *Saccharomyces cerevisiae* . . . ", Metabolic Engineering 2005.
Datta et al., "Technological and economic potential of poly(lactic acid) and lactic acid derivatives," FEMS Microbioal Rev., 1995, vol. 16, pp. 221-231.
Kurtzman and Robnett, "Phylogenetic Relationships among yeasts . . . " FEMS Yeast Research 3 (2003) 417-432.
Kurtzman, "Phylogenetic circumscription of *Saccharomyces* . . . ", FEMS Yeast Research 4 (2003) 233-245.
Kurtzman; Robnett, "Identification and Phylogeny of Ascomycetous Yeasts from Analysis of Nuclear Large Subunit (26S) Ribosomal DNA Partial Sequences", Antonie Van Leeuwenhoek, (1998), vol. 73, pp. 331-371.
Langkjaer et al., Nature 421:848-852, 2003.
Liden et al., "A Glycerol-2-Phosphase Dehydrogenase-Deficient Mutant of *Saccharomyces cerevisiae* Expressing the Heterologous XYL1 Gene," Applied and Environmental Microbiology, vol. 62, No. 10, Oct. 1996, pp. 3894-3896.
Manolis Kellis et al., "Proof and evolutionary analysis of ancient genome duplication in the yeast *Saccharomyces cerevisiae*", Nature, vol. 428, pp. 617-624, 2004.
Merico et al., "Fermentative lifestyle in yeasts . . . ", FEBS Journal 274 (2007) 976-989.
Mueller, P.R.; Wold, B., "In vivo footprinting of a muscle specific enhancer by ligation mediated PCR.", Science, (1989), vol. 246, doi:doi:10.1126/science.2814500, pp. 780-786, XP000199111.
Nissen et al., "Anaerobic and aerobic batch cultivations of *Saccharomyces cerevisiae* . . . ", Yeast 16 (2000) 463-474.
Ostergaard et al., "Metabolic Engineering of *Saccharomyces cerevisiae*", Microbiology and Molecular Biology Review 64 (2000) 34-50.
Peter M. Bruinenberg, Johannes P. Van Dijken and W. Alexander Scherfferes, 1983, An Enzymatic Analysis of NADPH Production and Consumption in Candida utilis, J. General Microbiology vol. 129, pp. 965-971.
T.B. Vickroy, vol. 3, Chapter 38 of Comprehensive Biotechnology, (ed. M. Moo-Young), Pergamon, Oxford, 1985.
Traff et al.,"Deletion of the GRE3 Aldose Reductase Gene and Its Influence on Xylose Metabolism in Recombinant Strains of *Saccharomyces cerivisiae* Expressing the xylA and XKS1 Genes", Applied and Environmental Microbiology Dec. 2001, vol. 67, No. 21.
Wolfe et al., "Molecular evidence for an ancient duplication of the entire yeast genome", Nature 387, 708-713 (1997).

* cited by examiner

YEAST CELLS HAVING DISRUPTED PATHWAY FROM DIHYDROXYACETONE PHOSPHATE TO GLYCEROL

This application is a Continuation of U.S. patent application Ser. No. 15/941,274, filed 30 Mar. 2018 (now Granted as U.S Pat. No. 10,899,544), which is a Divisional of U.S. patent application Ser. No. 14/720,899, filed 25 May 2015 (now abandoned), which is a Divisional of U.S. patent application Ser. No. 12/281,286, filed 29 Aug. 2008 (now abandoned), which is a national phase application of International Application No. PCT/US2007/06408, filed 13 Mar. 2007 (now abandoned), which claims priority to United States Provisional Application No. 60/781,674, filed 13 Mar. 2006, each of which are hereby incorporated by reference in its entirety.

This invention was made under contract no. DE-FC36-03G013145 with the United States Department of Energy. The U.S. Government has certain rights to this invention.

This invention relates to certain genetically modified yeast, and fermentation processes to produce lactic acid using those genetically modified yeast.

Yeast are used as biocatalysts in a number of industrial fermentations. There is an increasing interest in using yeast to ferment sugars to organic acids such as lactic acid. As more organic acid is produced in these fermentations, the fermentation medium becomes increasingly acidic. Most bacteria that produce these organic acids do not perform well in strongly acidic environments—they either do not survive under those conditions or else produce so slowly that the process becomes economically unviable. As a result, it becomes necessary to buffer the medium to maintain a higher pH. This causes difficulty in recovering the product in acid form. It is preferred to conduct the fermentation at a lower pH at which the product is partially or wholly in the acid form.

Yeast species have been considered as candidates for such low-pH fermentations. Many yeast species naturally ferment hexose sugars to ethanol, but few if any naturally produce significant yields of organic acids such as lactic acid. Accordingly, efforts have been made to genetically modify various yeast species to insert one or more genes that will enable the cell to produce lactic acid. In order to divert sugar metabolism from ethanol production to lactic acid production, these cells have also been genetically modified to disrupt or delete the native pyruvate decarboxylase (PDC) gene. This work is described, for example, in WO 99/14335, WO 00/71738 A1, WO 02/42471 A2, WO 03/049525 A2, WO 03/102152 A2 and WO 03/102201 A2.

Glycerol is produced in significant yield in many of these yeast fermentations. Glycerol may serve as an osmoprotectant for the cell. Glycerol formation may help regenerate redox cofactors under fermentation conditions.

Glycerol is produced in many yeast cells by metabolizing dihydroxyacetone phosphate (DHAP). In most yeast species, DHAP is reduced by a glycerol-3-phosphate dehydrogenase (GPD, systematic name sn-glycerol-3-phosphate:NAD+2-oxidoreductase, EC 1.1.1.8) enzyme to form glycerol-3-phosphate (G3P). G3P serves as a precursor for lipid biosynthesis as well as a glycerol precursor. G3P is dephosphorylated to glycerol by a glycerol-3-phosphatase enzyme (GPP, systematic name glycerol-1-phosphate phosphohydrolase, EC 3.1.3.21).

There exists an alternate pathway for glycerol production, which is important for some yeast, such as S. pombe. In this pathway, dihydroxyacetone phosphate is dephosphorylated into dihydroxyacetone by dihydroxyacetone phosphate phosphatase. Dihydroxyacetone is then converted into glycerol in conjunction with NADH oxidation by NADH+-dependent glycerol dehydrogenase (systematic name glycerol:NAD+ 2-oxidoreductase, EC 1.1.1.6).

Because glycerol production consumes carbon that could otherwise be used to produce a more desirable fermentation product, this glycerol production represents a significant source of yield loss. In addition, glycerol production comes at the expense of both ATP and NADH. This directs energy away from the production of biomass or the desired product. For both of these reasons, it would be desired to reduce or eliminate glycerol production by the cell. A further consideration is that the reduction or elimination of glycerol production could simplify recovery and purification of the desired product.

A *Saccharomyces cerevisiae* strain has been genetically engineered to delete its native GPD genes, thus depriving the cell of the GPD enzyme and preventing glycerol production. See Nissen et al., "Anaerobic and aerobic batch cultivations of *Saccharomyces cerevisiae* mutants impaired in glycerol synthesis", *Yeast*, 2000: 16:463-474. Nissen et al. report that the mutated cells grew very poorly under both anaerobic and aerobic conditions when both of the native GPD genes were disrupted.

According to Nissen et al., the mutated cells produced much less glycerol than the wild-type cells. Nissen et al. hypothesized that the poor growth seen in the double deletant strains was due to a depletion of the cell's $NAD^+$ pool, because glycerol production was not available to oxidize NADH in the cell.

It would be desirable to provide a yeast cell that produces a desired organic product, which produces little or no glycerol, and which also grows well under aerobic conditions, anaerobic conditions or both aerobic and anaerobic conditions.

In one aspect, this invention is a mutant yeast cell of a pre-whole genome duplication yeast species, having a deletion or disruption of a native metabolic pathway from dihydroxyacetone phosphate to glycerol. The deletion or disruption of the native metabolic pathway may include a deletion or disruption of at least one native glycerol-3-phosphate dehydrogenase (GPD) gene. The deletion or disruption of the native metabolic pathway may include a deletion or disruption of at least one native glycerol-3-phosphatase (GPP) gene. It may include a deletion or disruption of at least one native glycerol-3-phosphate dehydrogenase (GPD) gene and at least one native glycerol-3-phosphatase (GPP) gene. The deletion or disruption of the native metabolic pathway may include a deletion or disruption of at least one native dihydroxyacetone phosphate phosphatase gene, native glycerol dehydrogenase gene, or both.

In another aspect, this invention is a mutant yeast cell of of a pre-whole genome duplication yeast species, which mutant cell produces less than 2.0 g/L of glycerol when cultivated under the following standard microaerobic conditions:

A. defined aqueous medium containing, at the start of cultivation, 5 g/L ammonium sulfate, 3 g/L potassium dihydrogen phosphate, 0.5 g/L magnesium sulfate, trace elements, vitamins, 150 g/L glucose;

B. pH at the start of cultivation of 3.5, with fermentation medium being buffered if necessary to prevent the pH from falling below 3.0 or rising above 7.0 during the cultivation;

C. Cultivation inoculated with the yeast cell to an $OD_{600}$ of 1.0;

D. Cultivation temperature 30° C.;
E. Cultivation continued until glucose concentration is reduced to 10 g/L, but is not continued for more than 120 hours;
F. Aeration and agitation sufficient to produce an oxygen uptake rate of 5.0±1.0 mmol/L/hr.

In another aspect, this invention is a mutant yeast cell of a pre-whole genome duplication yeast species, which lacks the ability to produce an active glycerol-3-phosphate dehydrogenase (GDP) enzyme. For purposes of this invention, a cell is considered to lack the ability to produce an active enzyme if the activity of such enzyme in the cell is reduced by at least 75%, preferably at least 90%, compared to the activity of that enzyme in the wild-type strain. Enzyme activity of any particular enzyme can be determined using appropriate assay methods. Commercial assay kits are available for determining glycerol-3-phosphate dehydrogenase activity. An example of such a product is designated as MK426 by Takara Bio, Inc. and is available through Fisher Scientific, Pittsburgh, Pa.

In another aspect, this invention is a mutant yeast cell of a pre-whole genome duplication yeast species, which lacks the ability to produce an active glycerol-3-phosphatase enzyme.

In another aspect, this invention is a mutant yeast cell which lacks the ability to produce an active dihydroxyacetone phosphate phosphatase enzyme that is natively produced by wild type cells of the yeast species, lacks the ability to produce an active $NADH^+$-dependent glycerol dehydrogenase enzyme that is natively produced by wild type cells of the yeast species, or both In another aspect, this invention is a mutant yeast cell that is genetically modified to produce a product organic acid, said yeast cell further having a deletion or disruption of a native metabolic pathway from dihydroxyacetone phosphate to glycerol and a deletion or disruption of a native metabolic pathway from pyruvate to ethanol. The deletion or disruption of the native metabolic pathway may include a deletion or disruption of at least one native glycerol-3-phosphate dehydrogenase gene. The deletion or disruption of the native metabolic pathway may include a deletion or disruption of at least one native glycerol-3-phosphatase gene. It may include a deletion or disruption of at least one native glycerol-3-phosphate dehydrogenase gene and at least one native glycerol-3-phosphatase gene.

Cells in accordance with the invention have been found to produce very low levels of glycerol when cultivated under fermentation conditions. Glycerol production has been found to be below 0.2 g/L under a range of fermentation conditions. Surprisingly, the cells of the invention grow well under fermentation conditions, despite the lack of glycerol production and in some embodiments despite the lack of glycerol-3-phosphate production. The cells of the invention have also been found to have improved acid tolerance in some instances. Accordingly, the invention is also a fermentation process wherein a cell of any of the foregoing aspects of the invention is cultivated under fermentation conditions to produce a fermentation product, wherein the yield of carbon source to glycerol is less than 2% by weight.

Figure 2:
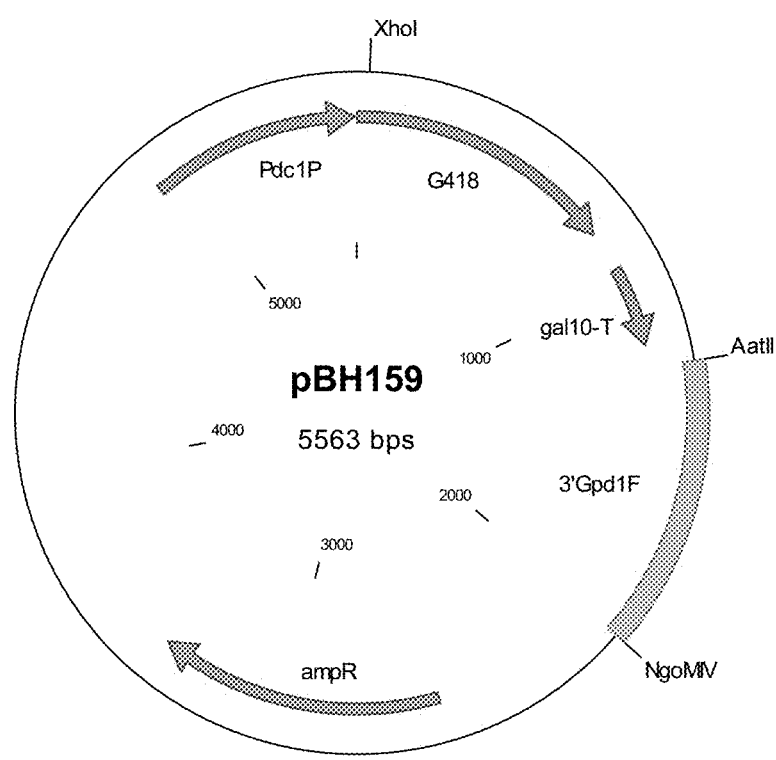
Figure 3:
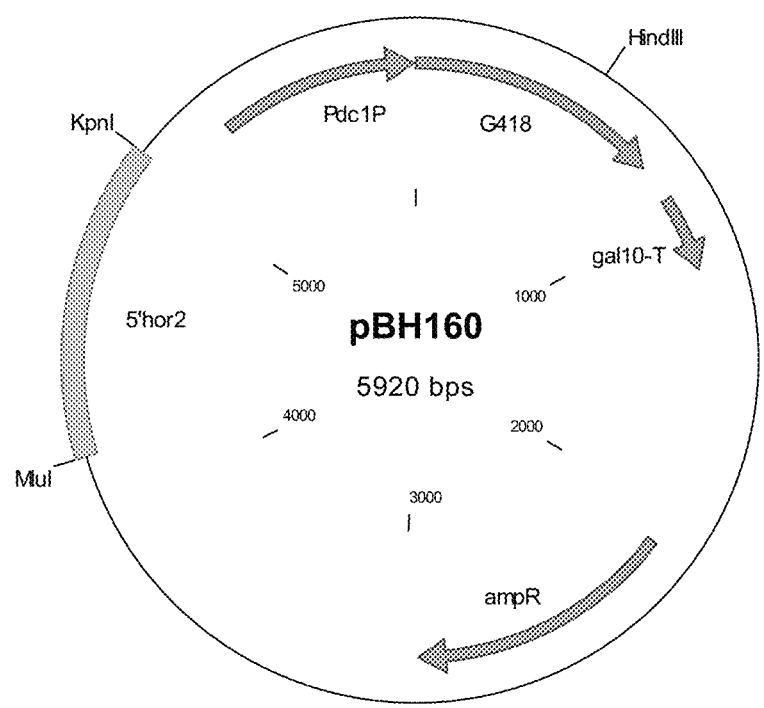
Figure 4:
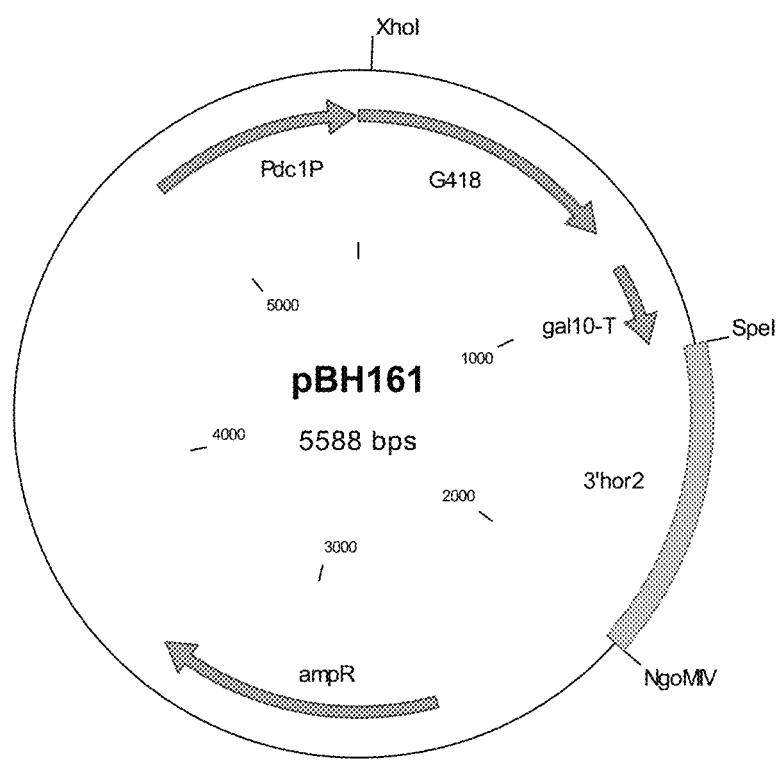
Figure 5:
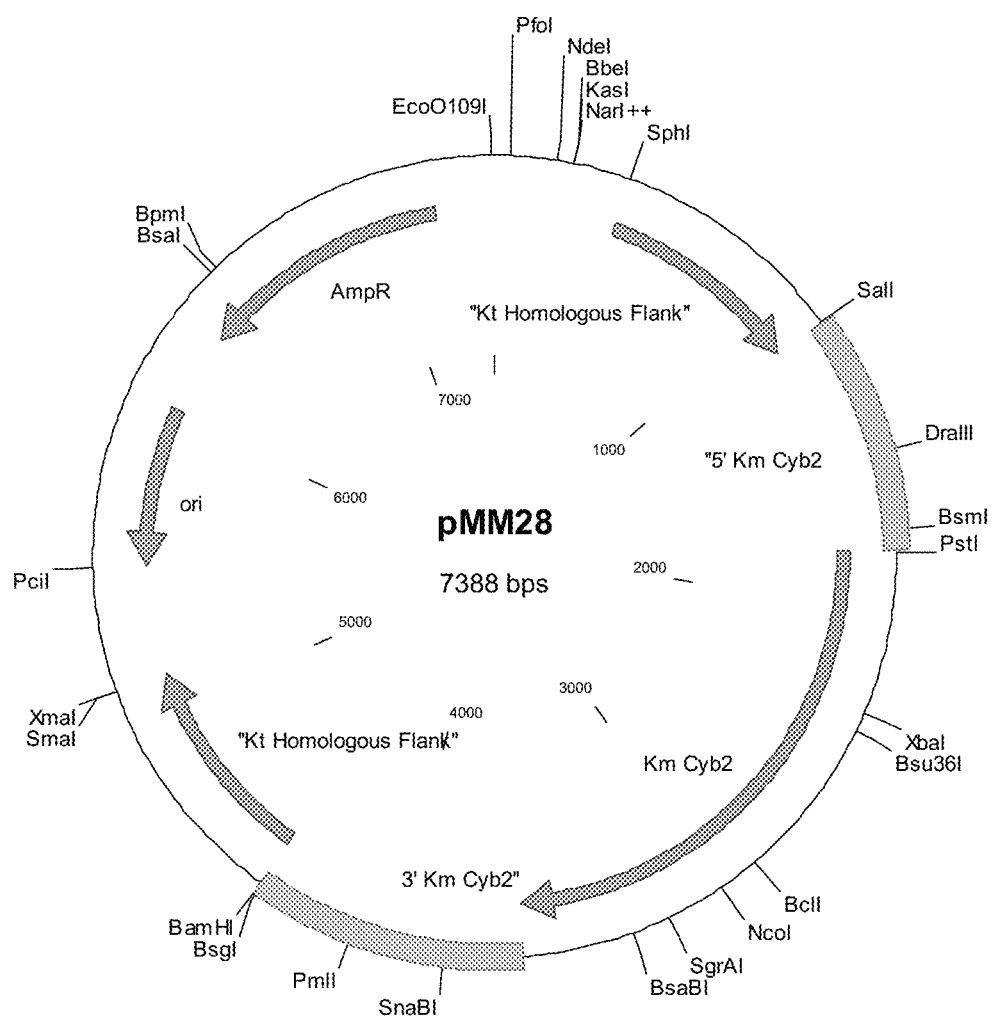
Figure 6:
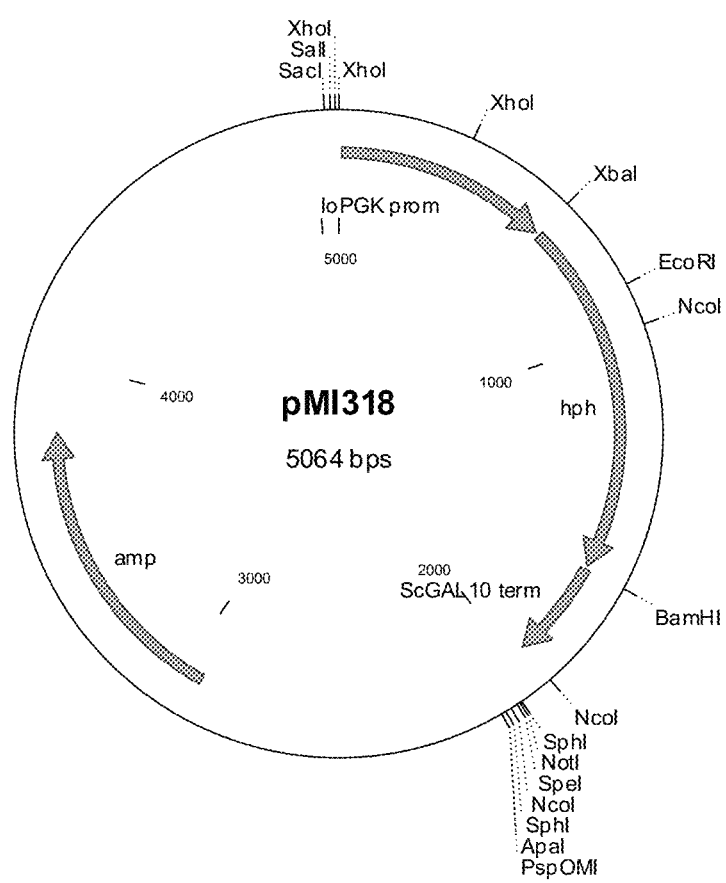
Figure 7:
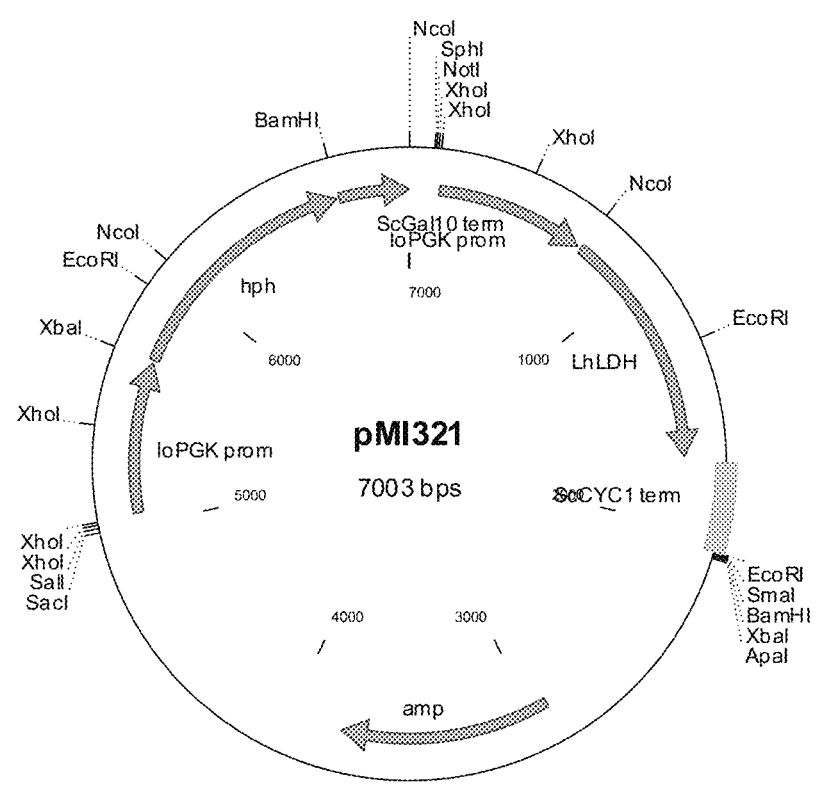
Figure 8:
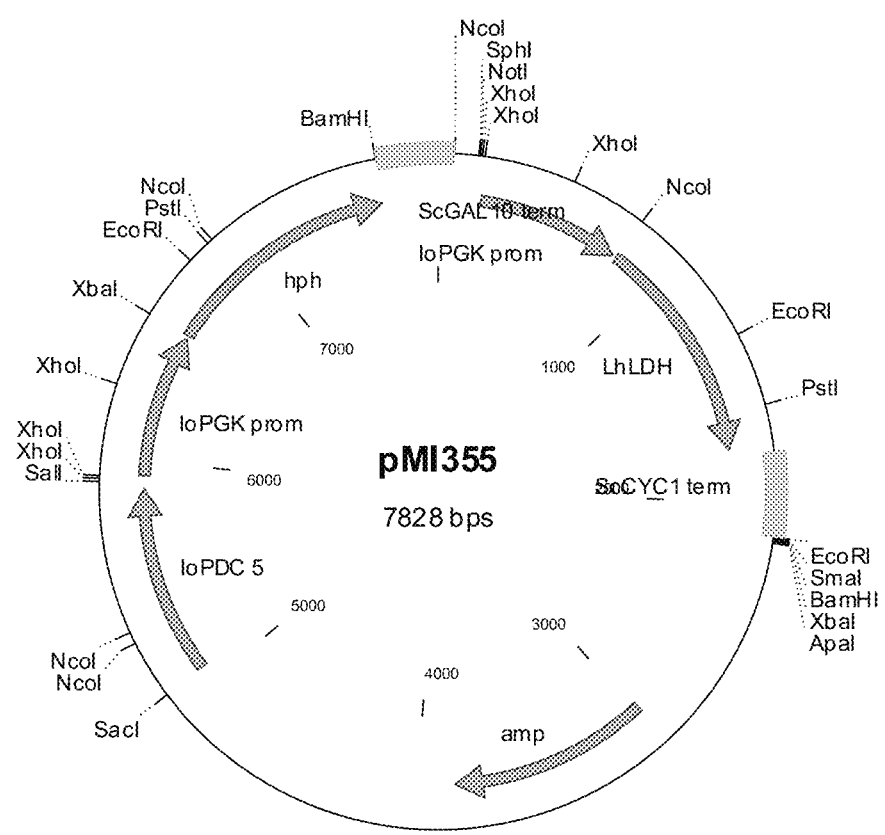
Figure 9:
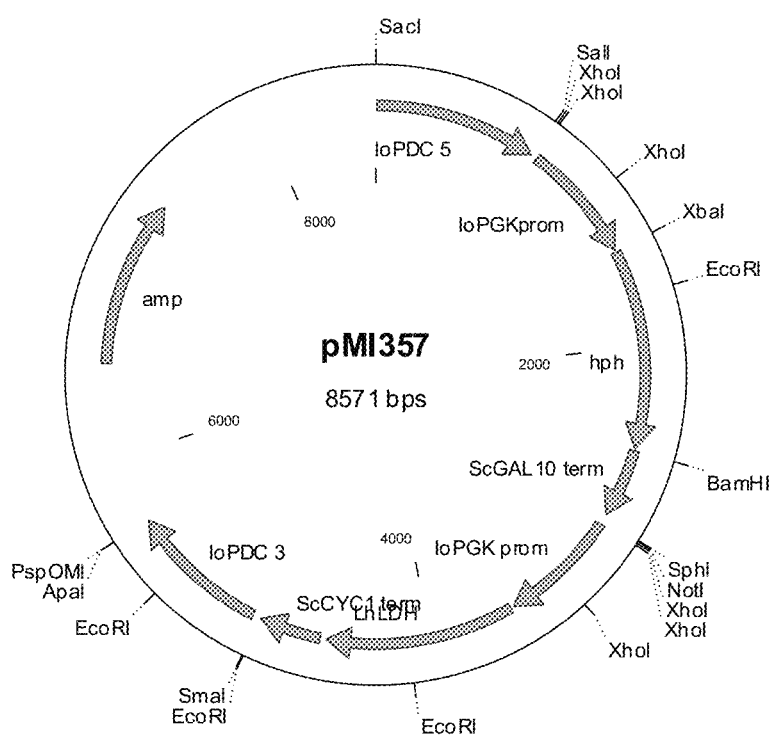
Figure 10:
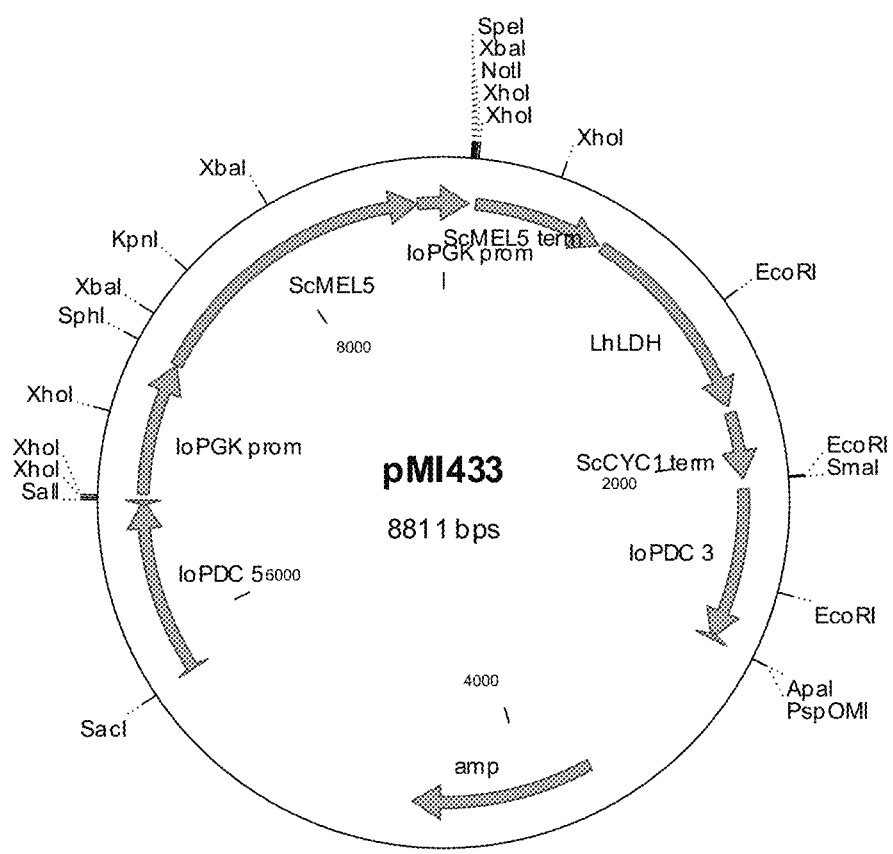
Figure 11:
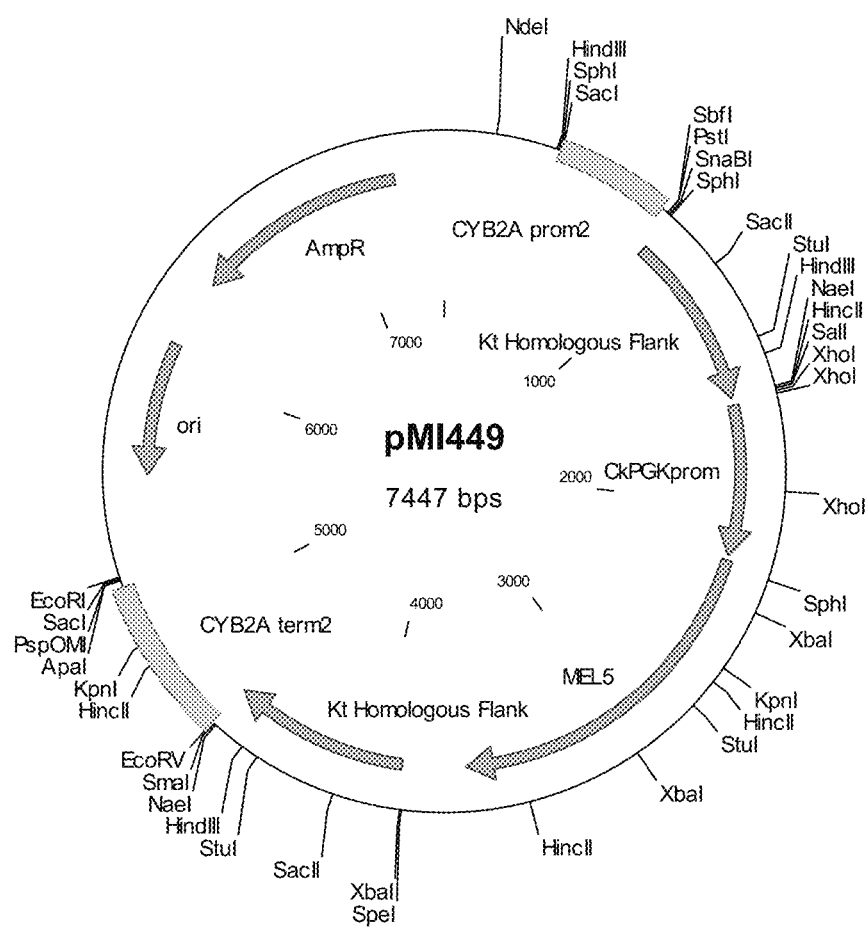
Figure 12:
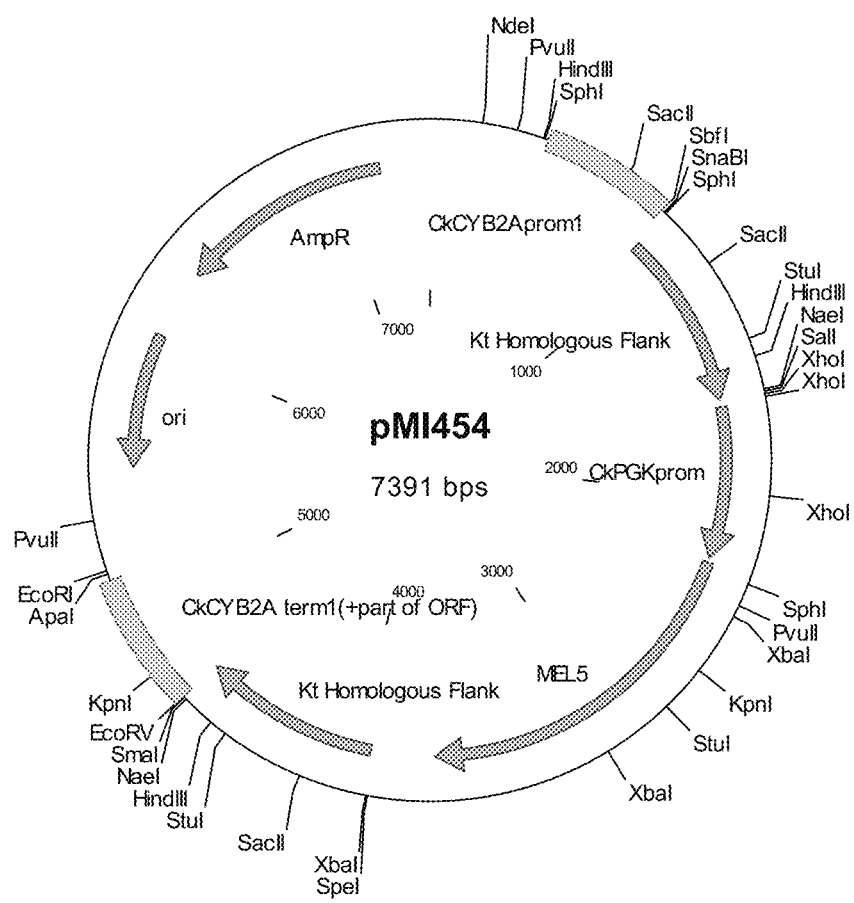
Figure 13:
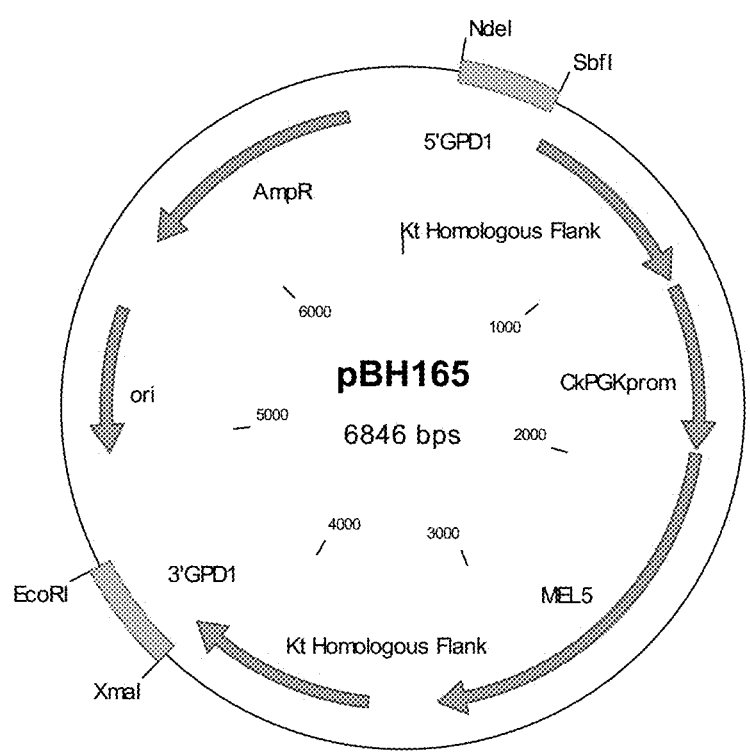
Figure 14:
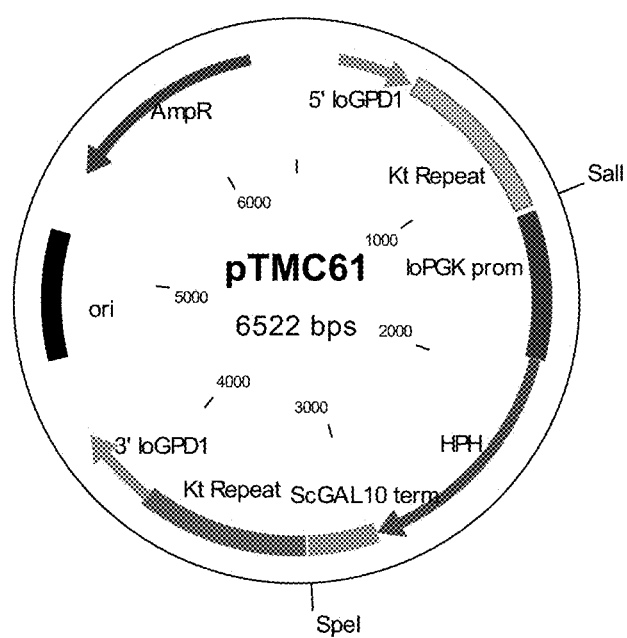

FIG. 1 is a diagram depicting the pBH158 plasmid.
FIG. 2 is a diagram depicting the pBH159 plasmid.
FIG. 3 is a diagram depicting the pBH160 plasmid.
FIG. 4 is a diagram depicting the pBH161 plasmid.
FIG. 5 is a diagram depicting the pMM28 plasmid.
FIG. 6 is a diagram depicting the pMI318 plasmid.
FIG. 7 is a diagram depicting the pMI321 plasmid.
FIG. 8 is a diagram depicting the pMI355 plasmid.
FIG. 9 is a diagram depicting the pMI357 plasmid.
FIG. 10 is a diagram depicting the pMI433 plasmid.
FIG. 11 is a diagram depicting the pMI449 plasmid.
FIG. 12 is a diagram depicting the pMI454 plasmid.
FIG. 13 is a diagram depicting the pBH165 plasmid.
FIG. 14 is a diagram depicting the pTMC61 plasmid.

The yeast cells of the invention are made by performing certain genetic modifications to a host yeast cell. The host yeast cell is one which, as a wild-type strain, is natively capable of metabolizing at least one sugar to glycerol. The native metabolic pathway may involve a metabolic pathway from dihydroxyacetone phosphate to glycerol-3-phosphate to glycerol. The native pathway may involve a metabolic pathway from dihydroxyacetone phosphate to dihydroxyacetone to glycerol. Host cells may contain both of those native metabolic pathways.

The term "native," when used herein with respect to genetic materials (e.g., a gene, promoter, terminator or other DNA sequence), refers to genetic materials that are found (apart from individual-to-individual mutations which do not affect function) within the genome of wild-type cells of that species of yeast. "Native capability" (and its variations such as "natively capable") indicates the ability of wild-type cells to perform the indicated function. For example, a cell is natively capable of metabolizing a sugar to glycerol if wild-type cells of that species possess that capability prior to any genetic modifications. A gene is considered to be "functional" within a cell if it functions within the cell to produce an active protein. A "native pathway" or "native metabolic pathway" refers to a metabolic pathway that exists and is active in wild-type cells of that species of yeast. An enzyme is "natively produced" by a yeast species if the enzyme is produced in active form by wild type cells of that species of yeast.

In this invention, "exogenous" means with respect to any genetic material that it is not native to the host cell.

Suitable host yeast cells for certain embodiments of the invention include yeast cells which are not descended from a line that underwent the ancient (~100 million years ago) whole genome duplication event described by Wolf et al., "Molecular evidence for an ancient duplication of the entire yeast genome", Nature 387, 708-713 (1997) (hereinafter "Wolf et al 1997"), Langkjaer et al., "Yeast genome duplication was followed by asynchronous differentiation of duplicated genes", Nature 421, 848-852 (2003) and Merico et al., "Fermentative lifestyle in yeasts belonging to the Saccharomyces complex", FEBS Journal 274, 967-989 (2007) (hereinafter "Merico 2007"). Such yeast cells are instead descended from one or more other lines of yeast cells that existed at the time of the whole genome duplication event, and are referred to herein as "pre-whole genome duplication yeast". The whole genome duplication event is seen as critical for the evolution of the fermentative capabilities of *Saccharomyces cerevisiae* and other species descended from the common ancestor in which the genome duplication occurred (Merico 2007). Included in the set of genes duplicated in the genome duplication are those encoding glycerol-3-phosphate dehydrogenase and glycerol-3-phosphatase, as are genes encoding fumarate reductase which is also involved in maintaining redox balance (Wolfe et al 1997).

Among the suitable pre-whole genome duplication yeast cells are hemiascomycetous yeast cells. Hemiascomycetous yeast are single-celled yeast classified within the order Saccharomycetales.

Other suitable yeast cells include those falling within any of the clades 7, 8, 9, 10, 11, 12, 13 or 14 of the Saccharomyces complex, as described in FIG. 9 (p. 430) of Kurtzman and Robnett, "Phylogenetic relationships among yeasts of the 'Saccharomyces complex' determined from multigene sequence analyses.", FEMS Yeast Res. Vol. 4, pp. 417-432. (2003), incorporated herein by reference. Those clades are designated by the names *Zygosaccharomyces, Zygotorulaspora, Torulaspora, Lachancea, Kluyveromyces, Eremothecium, Hanseniaspora* and *Saccharomycodes*, respectively, in Merico 2007, supra, and in Kurtzmann, "*Phylogenetic circumscription of Saccharomyces, Kluyveromyces and other members of the Saccharomycetaceae . . .* " *FEMS Yeast. Res.* Vol. 4, pp. 233-245 (2003) (hereinafter "Kurtzman 2003").

Other suitable yeast cells include (but are not limited to) yeast cells classified under the genera *Candida, Saccharomyces, Schizosaccharomyces, Kluyveromyces, Pichia, Issatchenkia,* and *Hansenula*.

A class of host cells that are of particular interest includes any of those of a species contained within the *I. orientalis/I. terricola* clade. Members of the *I. orientalis/I. terricola* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences", Antonie van Leeuwenhoek 73:331-371, 1998, incorporated herein by reference (hereinafter "Kurtzman and Robnett 1998"). See especially p. 349 and 361. Analysis of the variable D1/D2 domain of the 26S ribosomal DNA from hundreds of ascomycetes has revealed that the *I. orientalis/I. terricola* clade contains closely related species. Members of the *I. orientalis/I. terricola* clade exhibit greater similarity in the variable D1/D2 domain of the 26S ribosomal DNA to that of other members of the clade than to that of yeast species outside of the cladea. Therefore, other members of the *I. orientalis/I. terricola* clade can be identified by comparison of the D1/D2 domains of their respective ribosomal DNA and comparing to that of other members of the clade and closely related species outside of the clade, using Kurtzman and Robnett's methods. Yeast species within the *I. orientalis/I. terricola* clade are all hemiascomycetous yeast within the broader *Pichia/Issatchenkia/Saturnispora/Dekkera* clade. Another class of host cells of interest is the *I. orientalis/P. fermentans* clade as described by Kurtzman and Robnett 1998. That clade is the most terminal clade that contains at least the species *Issatchenkia orientalis, Pichia galeiformis, Pichia* sp. YB-4149 (NRRL designation), *Candida ethanolica, P. deserticola, P. membranifaciens* and *P. fermentans*.

Other host cells of particular interest are any of those of a species contained within the *Kluyveromyces* clade of *Saccharomyces* complex, as described (as Clade 11) in FIG. 9 (p. 430) of Kurtzman and Robnett, "Phylogenetic relationships among yeasts of the '*Saccharomyces* complex' determined from multigene sequence analyses.". FEMS Yeast Res. Vol. 4, pp. 417-432. (2003), incorporated herein by reference, and in FIG. 1 of Kurtzmann, "*Phylogenetic circumscription of Saccharomyces, Kluyveromyces and other members of the Saccharomycetaceae . . .* " *FEMS Yeast. Res.*, Vol. 4, pp. 233-245 (2003) (hereinafter "Kurtzman 2003"), incorporated herein by reference. The *Kluyveromyces* clade includes at least the species *S. kluyveri, K. aestuaryii, K. nonfermentans, K. lactic, K. marxianus* and *K. dobzhanskii*, and would include additional species classifiable within that clade using the multigene sequene analysis methods described in Kurtzman 2003.

Such yeast cells are of particular interest when genetically modified to produce an organic acid, especially lactate. Host cells from the *Candida, Kluyveromyces* and *Ittatchenkia* genera are generally preferred. Host cells from the *Kluyveromyces* and *I. orientalis/P. fermentans* clades described before are particularly preferred, in those embodiments where the mutant cell produces an organic acid, as well as in cases where the mutant cell produces another fermentation product (such as, for example, ethanol) in addition to or instead of an organic acid. Especially preferred host cells are *C. sonorensis, K. marxianus, K. thermotolerans, C. methanosorbosa,* and *I. orientalis*. Most preferred cells are *K. marxianus, C. sonorensis,* and *I. orientalis*. When first characterized, the species *I. orientalis* was assigned the name *Pichia kudriavzevii*. The anamorph (asexual form) of *I. orientalis* is known as *Candida krusei*. Suitable strains of *K. marxianus* and *C. sonorensis* include those described in WO 00/71738 A1, WO 02/42471 A2, WO 03/049525 A2, WO 03/102152 A2 and WO 03/102201A2. Suitable strains of I. orientalis are ATCC strain 32196 and ATCC strain PTA-6648.

By "deletion or disruption" of a metabolic pathway, it means that the pathway is either rendered completely inoperative, or else its activity is reduced by at least 75%, preferably at least 90%, relative to the wild-type cell. Activity of a pathway may be reduced by reducing the amount of active enzyme that is produced, by reducing the activity of the enzyme that is produced, or some combination of both. By "deletion or disruption" of a gene it is meant that the entire coding region of the gene is eliminated (deletion), or the coding region of the gene, its promoter, and/or its terminator region is modified (such as by deletion, insertion, or mutation) so that the gene no longer produces an active enzyme, the gene produces a severely reduced quantity (at least 75% reduction, preferably at least 90% reduction) of the active enzyme, or the gene produces an enzyme with severely reduced (at least 75% reduced, preferably at least 90% reduced) activity.

In most cases, the deletion or disruption of the native metabolic pathway will involve a deletion or disruption of at least one GPD gene, at least one GPP gene, or both. In cells such as *S. pombe*, that have an alternate metabolic pathway based on dihydroxyacetone phosphate phosphatase and glycerol dehydrogenase, the deletion or disruption of the native metabolic pathway will usually include a deletion or disruption of the dihydroxyacetone phosphate phosphatase gene, glycerol dehydrogenase gene, or both. In cells having both pathways, deletions or disruptions of both pathways can be performed.

The term "glycerol-3-phosphate dehydrogenase gene" and "GPD gene" are used herein to refer to (a) any gene that encodes for a protein with glycerol-3-phosphate dehydrogenase activity and/or (b) any chromosomal DNA sequence that encodes for an enzyme that is at least 50%, preferably at least 60% and more preferably at least 65% identical to any of the amino acid sequences identified as SEQ. ID. NO. 1, SEQ. ID. NO. 2, SEQ. ID. NO. 3, SEQ. ID. NO. 4, SEQ. ID. NO. 5, SEQ. ID. NO. 6, or SEQ. ID. NO. 7. "Glycerol-3-phosphate dehydrogenase activity" refers to the ability of a protein to catalyze the reaction of DHAP to glycerol-3-phosphate. For purposes of this invention, percent identity of amino acid sequences of DNA, RNA or proteins can conveniently computed using BLAST (NCBI Basic Local Alignment Search Tool) version 2.2.1 software with default parameters. Sequences having an identities score of at least XX %, using the BLAST version 2.2.13 algorithm with default parameters, are considered at least XX % identical.

The BLAST software is available from the National Center for Biological Information, Bethesda, Md.

Similarly, "glycerol-3-phosphatase gene" and "GPP gene" are used herein to designate (a) any gene that encodes for a protein with glycerol-3-phosphatase activity and/or (b) any chromosomal DNA sequence that encodes for a protein that is at least 50%, preferably at least 60% and more preferably at least 65% identical to any of the amino acid sequences identified as SEQ. ID. NO.8, SEQ. ID. NO. 9, SEQ. ID. NO. 10, SEQ. ID. NO 11 or SEQ. ID. NO 12. "Glycerol-3-phosphatase activity" refers to the ability of a protein to catalyze the dephosphorylation of glycerol-3-phosphate to form glycerol.

The term "dihydroxyacetone phosphate phosphatase" gene is used herein to denote any gene that encodes for a protein with dihydroxyacetone phosphate phosphatase activity. "Glycerol dehydrogenase" gene is used herein to denote (a) any gene coding for a protein with glycerol dehydrogenase activity and/or (b) any chromosomal DNA sequence that encodes for a protein that is at least 50%, preferably at least 60% and more preferably at least 65% identical to the amino acid sequence identified as SEQ. ID. NO. 13. "Dihydroxyacetone phosphate phosphatase activity" refers to the ability of a protein to catalyze the reaction of dihydroxyacetone phosphate to dihydroxyacetone. "Glycerol dehydrogenase activity" refers to the ability of a protein to catalyze the reduction of dihydroxyacetone to glycerol.

The deletion or disruption of any of the foregoing genes can be accomplished by forced evolution, mutagenesis, or genetic engineering methods, followed by appropriate selection or screening to identify the desired mutants.

In mutagenesis methods cells are exposed to ultraviolet radiation or a mutagenic substance, under conditions sufficient to achieve a high kill rate (60-99.9%, preferably 90-99.9%) of the cells. Surviving cells are then plated and selected or screened for cells having the deleted or disrupted metabolic activity. Cells having the desired mutation can be screened for on the basis of their reduced ability to produce glycerol. Disruption or deletion of any of the foregoing genes can be confirmed through PCR or Southern analysis methods.

Genetic engineering to delete or disrupt the metabolic pathway to glycerol is conveniently accomplished in one or more steps via the design and construction of appropriate deletion constructs and transformation of the host cell with those constructs. The term "construct" is used herein to denote a DNA sequence that is used to transform a cell. The construct may be, for example, in the form of a circular plasmid or vector, in the form of a linearized plasmid or vector, may be a portion of a circular plasmid or vector (such as is obtained by digesting the plasmid or vector with one or more restriction enzymes), or may be a PCR product prepared using a plasmid or vector as a template. Selection or screening follows to identify successful transformants. Electroporation and/or chemical (such as calcium chloride- or lithium acetate-based) transformation methods can be used.

The following discussion of deletion constructs is equally applicable to the deletion or disruption of any of the glycerol-3-phosphate dehydrogenase, glycerol-3-phosphatase, dihydroxyacetone phosphate phosphatase or glycerol dehydrogenase genes.

A deletion construct is conveniently assembled by first cloning two DNA sequences of the target gene and/or its upstream (5') or downstream (3') flanking regions. The sequences are preferably non-contiguous, but may be contiguous if additional genetic material (such as a selection marker cassette) is to be interposed between them on the construct. In this context, "non-contiguous" means that the DNA sequences are not immediately adjacent to each other in the wild-type genome, but instead are separated from each other in the wild-type genome by an area that is to be deleted in order to delete or disrupt the gene. "Contiguous" sequences are directly adjacent to each other in the wild-type genome. One of the sequences may include a region 5' to the promoter of the target gene, all or a portion of the promoter region, all or a portion of target gene coding region, or some combination thereof. The other sequence may include a region 3' to the terminator of the target gene, all or a portion of the terminator region, and/or all or a portion of the target gene coding region. A deletion construct is then produced containing the two sequences oriented in the same direction in relation to each other as they natively appear on the chromosome of the host cell. Typically a selection marker is cloned between the sequences to allow selection of transformants, as described more fully below. This construct is used to transform the host cell. Electroporation and/or chemical (such as calcium chloride- or lithium acetate-based) transformation methods can be used.

In successful transformants, a homologous recombination event at the locus of the target gene results in the disruption or the deletion of the functional gene. All or a portion of the native target gene, its promoter and/or terminator is deleted during this recombination event. If the deletion construct contains genetic material between the two sequences taken from the target locus (such as a selection marker cassette or structural gene cassette), that genetic material is inserted into the host cell's genome at the locus of the deleted material. Analysis by PCR or Southern analysis can be performed to confirm that the desired deletion has taken place.

It is usually desirable that the deletion construct may also include a functional selection marker cassette. When a single deletion construct is used, the marker cassette resides on the vector downstream (i.e., in the 3' direction) of the 5' sequence from the target locus and upstream (i.e., in the 5' direction) of the 3' sequence from the target locus. Successful transformants will contain the selection marker cassette, which imparts to the successfully transformed cell some characteristic that provides a basis for selection. A "selection marker gene" is one that encodes a protein needed for the survival and/or growth of the transformed cell in a selective culture medium. Typical selection marker genes encode proteins that (a) confer resistance to antibiotics or other toxins, (such as, for example, zeocin (*Streptoalloteichus hindustanus* ble bleomycin resistance gene), G418 (kanamycin-resistance gene of Tn903) or hygromycin (aminoglycoside antibiotic resistance gene from *E. coli*)), (b) complement auxotrophic deficiencies of the cell (such as, for example, amino acid leucine deficiency (*K. marxianus* LEU2 gene) or uracil deficiency (e.g., *K. marxianus* or *S. cerevisiae* URA3 gene)); (c) enable the cell to synthesize critical nutrients not available from simple media, or (d) confer ability for the cell to grow on a particular carbon source, (such as a MEL5 gene from *S. cerevisiae*, which encodes the alpha-galactosidase (melibiase) enzyme and confers the ability to grow on melibiose as the sole carbon source). Preferred selection markers include the zeocin resistance gene, G418 resistance gene, a MEL5 gene and hygromycin resistance gene. Another preferred selection marker is an L-lactate:ferricytochrome c oxidoreductase (CYB2) gene cassette, provided that the host cell either natively lacks such a gene or that its native CYB2 gene(s) are first deleted or disrupted.

The selection marker cassette will further include promoter and terminator sequences, operatively linked to the selection marker gene, and which are operable in the host cell. One suitable type of promoter is at least 50%, 70%, 90%, 95% or 99% identical to a promoter that is native to a yeast gene. A more suitable type of promoter is at least 50%, 70%, 90%, 95% or 99% identical to a promoter for a gene that is native to the host cell. Particularly useful promoters include promoters for pyruvate decarboxylase (PDC1), phosphoglycerate kinase (PGK), xylose reductase (XR), xylitol dehydrogenase (XDH), L-(+)-lactate-cytochrome c oxidoreductase (CYB2), translation elongation factor-1 (TEF1) and translation elongation factor-2 (TEF2) genes, especially from the respective genes of the host cell. An especially useful promoter includes the functional portion of a promoter for a PDC1, PGK, TEF1 or TEF2 gene native to the host cell, or a sequence that is at least 80, 85, 90 or 95% identical to such a PDC1, PGK, TEF1 or TEF2 promoter.

One suitable type of terminator is at least 50%, 70%, 90%, 95% or 99% identical to a terminator for a gene that is native to a yeast cell. The terminator may be at least 50%, 70%, 90%, 95% or 99% identical to a terminator for a gene that is native to the host cell. Particularly useful terminators include terminators for pyruvate decarboxylase (PDC1), xylose reductase, (XR), xylitol dehydrogenase (XDH), L-lactate:ferricytochrome c oxidoreductase (CYB2) or iso-2-cytochrome c (CYC) genes, or a terminator from the galactose family of genes in yeast, particularly the so-called GAL10 terminator. An especially preferred terminator includes a functional portion of a terminator for a GAL10 gene native to the host cell, or a sequence that is at least 80, 85, 90 or 95% identical to such a terminator.

The deletion construct may be designed so that the selection marker cassette can become spontaneously deleted as a result of a subsequent homologous recombination event. A convenient way of accomplishing this is to design the vector such that the structural gene cassette is flanked by direct repeat sequences. Direct repeat sequences are identical DNA sequences, native or not native to the host cell, and oriented on the construct in the same direction with respect to each other. The direct repeat sequences are advantageously about 50-1500 bp in length. It is not necessary that the direct repeat sequences encode for anything. This construct permits a homologous recombination event to occur. This event occurs with some low frequency, resulting in cells containing a deletion of the selection marker gene and one of the direct repeat sequences. It may be necessary to grow transformants for several rounds on nonselective media to allow for the spontaneous homologous recombination to occur in some of the cells. Cells in which the selection marker gene has become spontaneously deleted can be selected or screened on the basis of their loss of the selection characteristic imparted by the selection marker gene.

The target gene deletion construct may also contain a structural gene cassette, again located downstream of the 5' flanking region and upstream of the 3' flanking region, but preferably not within any selection marker cassette as may be present. Such a construct permits the simultaneous deletion of the target gene and insertion of a structural gene. By "structural gene", it is meant any gene that encodes for a protein, other than the target gene or a selection marker gene as described above. A wide variety of structural genes can be used, but those of particular interest to this invention are a gene that confers to the cell the ability to produce an organic acid, or a gene that confers to the cell the ability to consume a particular carbon source, such as a pentose sugar.

In cases in which a selection marker is used, the transformation can be performed with pair of deletion constructs instead of a single deletion construct. One of the pair will contain the first sequence from the locus of the target gene and a non-functional part of the marker gene cassette. The other of the pair will contain the second sequence from the locus from the target gene and another non-functional part of the marker gene cassette. The two parts of the marker gene cassette are selected that that together they form a complete cassette. The ends of each of the two parts of the marker gene cassette share a common sequence, i.e., a portion of the cassette is duplicated at the ends of each of the two parts. The cell is transformed with these simultaneously to perform the desired deletion or disruption, with the formation of a complete, functional marker or structural gene cassette. A proportion of the cells will homologously integrate both deletion constructs at the target locus, and will engage in a further homologous recombination event to reconstitute a functional selection gene cassette from the two non-functional fragments. Successful transformants can be selected for on the basis of the characteristic imparted by the selection marker.

When the cell's native metabolic pathway includes the dihydroxyacetone phosphate-to-glycerol-3-phosphate-to-glycerol pathway (via GDP and GPP enzymes), either the GDP gene(s) or GPP gene(s) may be deleted or disrupted. Both the GDP and the GPP genes may be deleted. In such a case, the deletion or disruption of both the GDP and GPP genes may be done simultaneously or sequentially in either order. If the cell contains multiple GDP or GPP genes, or multiple alleles of such genes, it is preferred to delete all of those which are functional in the cell. In cases in which the cell's native metabolic pathway includes the dihydroxyacetone phosphate-to-dihydroxyacetone-to-glycerol pathway (via dihydroxyacetone phosphate phosphatase and glycerol dehydrogenase), either the dihydroxyacetone phosphate phosphatase or glycerol dehydrogenase genes may be deleted or disrupted. Both the dihydroxyacetone phosphate phosphatase or glycerol dehydrogenase genes may be deleted or disrupted, which may be done simultaneously or sequentially, in which case this can be done either order. As before, multiple functional copies or alleles of such genes are preferably all deleted.

In certain aspects of the invention, the cell is capable of producing a desired organic acid (or its salt). This capability is manifested by an ability to convert at least 5%, such at least 10%, at least 50%, at least 70%, at least 80% or at least 90%, by weight of a carbon source to the desired organic acid when cultivated under at least one set of fermentation conditions. As few yeast cells have the native ability to produce such acids, the cell of the invention will in most cases contain at least one functional, exogenous gene that enables it to produce the acid.

Cells of particular interest produce lactate, by which it is meant lactic acid or a salt thereof. In such case, the cell of the invention contains at least one functional, exogenous lactate dehydrogenase (LDH) gene integrated into its genome. An LDH gene is one that encodes for a functional lactate dehydrogenase enzyme. A functional LDH enzyme is one that catalyzes the reduction of pyruvate to lactate. LDH genes are specific to the production of either L-LDH or D-LDH, which respectively enable the cell to produce either the L- or D-lactic acid enantiomer (or their salts). It is possible that the modified cell of the invention contains both L- and D-LDH genes, and thus is capable of producing both lactic acid enantiomers. However, it is preferred that only L- or only D-LDH genes are present, so the cell produces a more optically pure lactic acid product.

Suitable LDH genes include those obtained from bacterial, fungal, yeast or mammalian sources. Examples of specific L-LDH genes are those obtained from *L. helveticus, L. casei, B. megaterium, P. acidilactici* and bovine sources. Examples of specific D-LDH genes are those obtained from *L. helveticus, L. johnsonii, L. bulgaricus, L. delbrueckii, L. plantarum,* and *L. pentosus*. Functional genes that are identical or at least 80% identical to any of these L-LDH or D-LDH genes are suitable. The native genes obtained from any of these sources may be subjected to mutagenesis if necessary to provide a coding sequence starting with the usual eukaryotic starting codon (ATG), or for other purposes. A preferred L-LDH gene is that obtained from L. helveticus or one that is at least 80%, 85%, 90% or 95% identical to such gene. Another preferred L-LDH gene is that obtained from B. megaterium or one that is at least 80%, 85%, 90% or 95% identical to such gene. A preferred D-LDH gene is that obtained from *L. helveticus* or one that is at least 80%, 85%, 90% or 95% identical to such gene.

Particularly suitable LDH genes include those that encode for an enzyme with an amino acid sequence that is at least 60%, especially at least 80%, 85% or 95%, identical to SEQ. ID. NO. 45 of WO 03/049525 or compared with SEQ. ID. NO. 49 of WO 03/049525. Particularly suitable LDH genes also include those that encode an enzyme having a protein sequence that is at least 60%, 80%, 85% or 95% identical to SEQ ID. NO. 46 or 50 of WO 03/049525.

The transformed cell may contain a single LDH gene or multiple LDH genes, such as from 1 to 10 LDH genes, especially from 1 to 5 LDH genes. When the transformed cell contains multiple LDH genes, the individual genes may be copies of the same gene, or include copies of two or more different LDH genes. Multiple copies of the exogenous LDH gene may be integrated at a single locus (so they are adjacent to each other), or at several loci within the host cell's genome.

The exogenous LDH gene is under the transcriptional control of one or more promoters and one or more terminators, both of which are functional in the modified yeast cell. Suitable promoters and terminators are as described before with regard to the selection marker gene cassette, and are also described in WO 99/14335, WO 00/71738, WO 02/42471, WO 03/102201, WO 03/102152 and WO 03/049525. An especially useful promoter includes the functional portion of a promoter for a PDC1, PGK, TEF1, or TEF2 gene of the host cell or is at least 80%, 85%, 90% or 95% identical to such a promoter. An especially preferred terminator includes a functional portion of a terminator for a PDC1 gene of the host cell or is at least 80%, 85%, 90% or 95% identical thereto.

When multiple exogenous LDH genes are introduced into the host cell, it is possible for the different LDH genes to be under the control of different types of promoters and/or terminators.

The exogenous LDH gene may be integrated randomly into the host cell's genome or inserted at one or more targeted locations. Examples of targeted locations include the locus of a gene that is desirably deleted or disrupted, such as that of a PDC1 gene, a glycerol-3-phosphate dehydrogenase gene, a glycerol 3-phosphatase gene, a dihydroxyacetone phosphate phosphatase gene or a glycerol dehydrogenase gene. The exogenous LDH gene cassette may reside on a construct for the deletion or disruption of a glycerol-3-phosphate dehydrogenase, glycerol-3-phosphatase, dihydroxyacetone phosphate phosphatase or glycerol dehydrogenase gene, and in that manner be inserted into the locus of such a gene simultaneously with the deletion or disruption thereof.

Methods for transforming a yeast cell to introduce an exogenous LDH gene cassette are described in WO 99/14335, WO 00/71738, WO 02/42471, WO 03/102201, WO 03/102152 and WO 03/049525. Such methods are applicable to this invention.

The cell may also be modified to enable it to produce one or more other organic acids. For example, the cell may be transformed with an exogenous gene cassette that encodes for a functional beta-alanine/pyruvate aminotransferase enzyme, thus enabling the cell to produce 3-hydroxy propionic acid. Methods for accomplishing this are described in WO 2005/118719.

The genetically modified yeast cell of the invention may include additional genetic modifications that provide one or more desired attributes to the cells.

An additional modification of particular interest in some embodiments includes a deletion or disruption of pyruvate decarboxylase gene(s). This reduces the cell's ability to produce ethanol, which is particularly desirable in cases in which an organic acid such as lactate is the desired product. If the host cell contains multiple PDC genes, it is especially preferred to delete or disrupt all of the PDC genes, although it is possible to delete fewer than all such PDC genes. PDC deletion can be accomplished using methods analogous to those described in WO 99/14335, WO 02/42471, WO 03/049525, WO 03/102152 and WO 03/102201. PDC deletion can also be accomplished with simultaneous insertion of an LDH gene cassette or other structural or selection marker gene cassette. In a method of particular interest, (1) non-contiguous sequences from the locus of the PDC gene(s) are cloned, (2) a construct containing the non-contiguous sequences is produced, and (3) the host cell is transformed with the construct. A homologous recombination event results in a deletion or disruption of the functional PDC gene in a portion of the transformants. This can be repeated if necessary to delete or disrupt multiple PDC genes or alleles. In some yeast species, such as *I. orientalis*, multiple PDC genes or alleles exist that are closely homologous. It has been found that in at least some such instances non-contiguous sequences taken from the locus of either gene or allele can be used in the construct to delete or disrupt both of the PDC genes or alleles. The construct used to disrupt the PDC gene(s) may include one or more functional marker or structural gene cassettes inserted downstream of the 5' flanking portion of the native PDC gene and upstream of the 3' flanking portions of the native PDC gene. This approach allows for the deletion of the PDC gene and insertion of the functional gene cassette in a single transformation step.

Another additional modification of particular interest is one (or more) which individually or collectively confers to the cell the ability to ferment pentose sugars to desirable fermentation products. Among the latter type of modifications are (1) insertion of a functional xylose isomerase gene, (2) a deletion or disruption of a native gene that produces an enzyme that catalyzes the conversion of xylose to xylitol, (3) a deletion or disruption of a functional xylitol dehydrogenase gene and/or (4) modifications that cause the cell to overexpress a functional xylulokinase. Methods for introducing those modifications into yeast cells are described, for example, in WO 04/099381, incorporated herein by reference. Suitable methods for inserting a functional xylose isomerase gene, deleting or disrupting a native gene that produces an enzyme that catalyzes the conversion of xylose to xylitol, deleting or disrupting a functional xylitol dehydrogenase gene modifying the cell to overexpress a functional xylulokinase are described, for example, in WO 04/099381, incorporated herein by reference.

Another additional modification of particular interest in lactate-producing cells of the invention includes a deletion or disruption of at least one L- or D-lactate:ferricytochrome c oxidoreductase gene.

In general, the cell of the invention is characterized by a reduced ability to synthesize glycerol. A useful method for evaluating a cell's ability to synthesize glycerol is by cultivating the cell under the standard microaerobic conditions described before. A defined aqueous fermentation medium is used, which contains at the start of cultivation 5 g/L ammonium sulfate, 3 g/L potassium dihydrogen phosphate, 0.5 g/L magnesium sulfate, trace elements, vitamins and 150 g/L glucose. The pH is adjusted to 3.5 at the start of cultivation. The pH is permitted to range freely during the cultivation, except that the medium is buffered if necessary to prevent the pH from falling below 3.0 or rising above 7.0 during the cultivation. The fermentation medium is inoculated with sufficient yeast cells that are the subject of the evaluation to produce an $OD_{600}$ of 1.0. The cultivation temperature is 30° C. The cultivation is continued until the glucose concentration is reduced to 5 g/L, but is not continued for more than 120 hours During the cultivation, aeration and agitation conditions are selected to produce an oxygen uptake rate of 5.0±1.0 mmol/L/hr. Under these standard conditions, the cells of the invention typically produce no more than 2.0 g/L of glycerol. More typically, they produce no more than 0.6 g/L of glycerol under these conditions and in most cases produce no more than 0.2 g/L of glycerol under these conditions. Preferred cells also produce, under these standard microaerobic conditions, at least 10 g/L of at least one desirable fermentation product, such as ethanol or an organic acid such as lactate. The cells more preferably produce at least 40 and especially at least 50 g/L of the desired fermentation produce under these conditions.

The cell of the invention can be cultivated, under the standard microaerobic conditions described before or any other useful set of fermentation conditions, to produce one or more desirable fermentation products. Ethanol is an example of a fermentation product which many yeast species produce naturally. As discussed before, the cells can be modified to enable them to produce other desirable fermentation products, including organic acids such as lactate or 3-hydroxy propionic acid. The cells may be modified to produce other fermentation products as well, including other acids or other products that are not acids.

In the fermentation process of the invention, the cell of the invention is cultivated in a fermentation medium that includes a carbon source that is fermentable by the transformed cell. The carbon source may be a hexose sugar such as glucose, or an oligomer or other polymer of glucose such as glycan, maltose, maltotriose or isomaltotriose. The carbon source may be another hexose sugar, of which panose, fructose, fructose and their respective oligomers and polymers are examples. If the cell natively has or is modified to impart an ability to ferment pentose sugars, the carbon source may include a pentose sugar such as xylose, or a xylose oligomer or polymer such as xylan. Such pentose sugars are suitably hydrolysates of a hemicellulose-containing biomass. In case of oligomeric sugars, it may be necessary to add enzymes to the fermentation broth in order to digest these to the corresponding monomeric sugar for fermentation by the cell.

The medium will typically contain nutrients as required by the particular cell, including a source of nitrogen (such as amino acids, proteins, inorganic nitrogen sources such as ammonia or ammonium salts, and the like), and various vitamins, minerals and the like. A so-called "complex" medium or a so-called "defined" medium can be used.

Other fermentation conditions, such as temperature, cell density, selection of substrate(s), selection of nutrients, and the like are not considered to be critical to the invention and are generally selected to provide an economical process. Temperatures during each of the growth phase and the production phase may range from above the freezing temperature of the medium to about 50° C., although this depends to some extent on the ability of the strain to tolerate elevated temperatures. A preferred temperature, particularly during the production phase, is from about 30-45° C.

During the production phase, the concentration of cells in the fermentation medium is typically in the range of from 0.1 to 20, preferably from 0.1 to 5, even more preferably from 1 to 3 g dry cells/liter of fermentation medium. The fermentation may be conducted aerobically, microaerobically, or anaerobically. If desired, oxygen uptake rate can be used as a process control, as described in WO 03/102200. Cells of the invention can perform especially well when cultivated under microaerobic conditions characterized by an oxygen uptake rate of from 4 to 12, especially from 5 to 10, mmol/L/hr.

In preferred cases in which the cell produces an organic acid such as lactate, the medium may be buffered during the production phase of the fermentation so that the pH is maintained in a range of about 3.5 to about 9.0, or from about 4.5 to about 7.0. Suitable buffering agents are basic materials that neutralize the acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

In a buffered fermentation, acidic fermentation products are neutralized to the corresponding salt as they are formed. Recovery of the acid therefore involves regenerating the free acid. This is typically done by removing the cells and acidulating the fermentation broth with a strong acid such as sulfuric acid. A salt by-product is formed (gypsum in the case where a calcium salt is the neutralizing agent and sulfuric acid is the acidulating agent), which is separated from the broth. The acid is then recovered from the broth through techniques such as liquid-liquid extraction, distillation, absorption, etc., such as are described in T. B. Vickroy, Vol. 3, Chapter 38 of *Comprehensive Biotechnology*, (ed. M. Moo-Young), Pergamon, Oxford, 1985; R. Datta, et al., FEMS Microbiol. Rev., 1995, 16:221-231; U.S. Pat. Nos. 4,275,234, 4,771,001, 5,132,456, 5,420,304, 5,510,526, 5,641,406, and 5,831,122, and WO 93/00440.

Alternatively, the pH of the fermentation medium may be permitted to drop during the cultivation from a starting pH that is above the pKa of the product acid, typically 5.5 or higher, to at or below the pKa of the acid fermentation product, such as in the range of about 1.5 to about 3.5, in the range of from about 1.5 to about 3.0, or in the range from about 1.5 to about 2.5.

It is also possible to conduct the fermentation to produce a product acid by adjusting the pH of the fermentation broth to at or below the pKa of the product acid prior to or at the start of the fermentation process. The pH may thereafter be maintained at or below the pKa of the product acid throughout the cultivation, or may be allowed to increase to above the pKa of the acid as the fermentation proceeds. In the former case, the pH is preferably maintained within the range of about 1.5 to about 3.5, in the range of about 1.5 to about 3.2, or in the range of about 2.0 to about 3.0.

The cell of the invention has a sharply reduced ability to produce glycerol under many fermentation conditions. The reduced ability of the cell to produce glycerol is manifested by low glycerol yields. The cells of the invention typically metabolize less than 2% by weight of the carbon source that is consumed to glycerol. In most cases, the glycerol yield is less than 1% or even less than 0.1%, based on the weight of carbon source that is consumed in the cultivation. Preferably, the cell metabolizes at least 40%, such as at least 50, 60, 70, 80 or 85%, of the carbon source that is consumed to the desired fermentation product.

It has been found that the cells of the invention exhibit good ability to grow under fermentation conditions. This is surprising, because of the cell's various uses for glycerol and the role glycerol is believed to play in balancing NADH/NAD$^+$ in wild-type yeast cells. It is within the scope of the invention to add glycerol to the fermentation medium to compensate for the cell's diminished capacity to produce glycerol on its own. However, applicants have found that doing this provides little benefit, at least in some fermentation processes.

The following examples are provided to illustrate the invention, but are not intended to limit the scope thereof. All parts and percentages are by weight unless otherwise indicated.

EXAMPLE 1A

Mutagenesis of *K. marxianus* Strain CD607 and Selection of Mutant Strain (CD853) having Resistance to Glycolic Acid

*K. marxianus* strain CD607 is described in Example 3D of WO 03/102152. This stain has a deletion of its pyruvate decarboxylase gene and an insertion of an exogenous lactate dehydrogenase gene at that locus. Cells of strain CD607 are subjected to mutagenesis via exposure to ultraviolet light.

Cells from a fresh YP (yeast extract plus peptone)+20 g/L glucose plate are resuspended in 2 mL of yeast peptone+50 g/L glucose to an approximate OD$_{600}$ of 6. Ten 125 µl aliquots of this cell suspension are pipeted into ten wells of a 300 µl 96-well microtiter plate. The microtiter plate is exposed to 12,500 µJoule/cm$^2$ of UV light to kill 90-99% of the cells. The microtiter plate is then incubated in darkness overnight at 30° C. with agitation (225 rpm) to allow the cells to recover prior to plating onto selection plates.

100 µl of the UV-treated cell suspensions are then plated onto a potato dextrose agar (PDA)+15 g/L glycolic acid plate to select for glycolic acid-resistant strains. These plates are incubated at 30° C. for several days until colonies appear. A single colony is isolated for further analysis.

Approximately 2×10$^8$ of mutagenized cells are plated onto PDA plates containing 15 g/L glycolic acid and incubated at 30° C. Colonies that grow on these plates are grown overnight in baffled shake flasks at 30° C. and 225 rpm agitation in YP (yeast peptone)+100 g/L glucose without buffer. Production flasks are then inoculated with 2 g/L cell dry weight from these shake flasks. The production flasks are cultured at 30° C. and 70 rpm agitation in YP+50 g/L glucose. Samples are withdrawn periodically to measure glucose, lactate, ethanol and pyruvate by HPLC using methods such as described in Example 1M of WO 03/102201. A strain that produces about 26 g/L lactate after 88 hours is designated as strain CD635. Strain CD635 is able to grow on lactate as the sole carbon source.

Cells of strain CD635 are subjected to an additional mutagenesis step as described above. The resulting mutagenized cells are selected for colonies that are able to grow on PDA containing 25 g/L glycolic acid. Colonies that are resistant to glycolic acid are separately grown overnight in YP+100 g/L glucose in shake flasks at 30° C. and 250 rpm agitation. Biomass is collected by centrifugation and 2 g/L dry weight of cells are inoculated into 50 mL YP+50 g/L glucose in a baffled shake flask. The flasks are cultivated at 30° C. and 250 rpm agitation for approximately 92 hours. A mutant that produces significantly higher final lactate titers, compared to parent strains CD607 and CD635, is designated as strain CD853.

Strain CD853 is unable to grow on lactate as the sole carbon source, suggesting that the native L-lactate:ferricytochrome c oxidoreductase gene (KmCYB2) gene has become non-functional in this mutant. Therefore, the KmCYB2 coding region plus ~500 bp up and downstream from the KmCYB2 coding region is amplified from this strain, using PCR with high fidelity FailSafe enzyme and genomic DNA as the template. The resulting ~2.75 kbp PCR product is purified via Qiagen column purification and sequenced over the entire KmCYB2 coding region. Strain CD853 is found to have a four-base insertion at amino acid position 62 of the KmCYB2 gene, which causes a frameshift mutation, resulting in a stop codon at amino acid position 76 and truncating the protein.

EXAMPLE 1B

Construction of GPD1F Deletion Vectors pBH158 (FIG. 1) and pBH159 (FIG. 2)

A plasmid designated pVR29 (described in Example 1C and FIG. 4 of WO 03/102152) contains the kanamycin-resistance gene of Tn903 (G418 gene) under the control of a pyruvate decarboxylase promoter and a GAL10 terminator. Plasmid pVR29 is digested with MluI and PstI and a 5.1 kbp fragment containing the G418 gene cassette so obtained is gel purified and dephosphorylated. A 1.2 kbp region of DNA upstream of the *K. marxianus* GPD (KmGPD1F) gene is amplified by PCR using primers identified as SEQ. ID. NO. 14 and SEQ. ID. NO. 15, with *K. marxianus* genomic DNA as a template. The PCR product is gel purified, digested with MluI and PstI, and ligated to the 5.1 kbp fragment from plasmid pVR29 to produce a plasmid designated as pBH158 (FIG. 1). Plasmid pBH158 contains, in order of transcription, the 1.2 kbp upstream flank of the KmGPD1F gene and the G418 expression cassette.

For the second deletion vector, plasmid pVR29 is digested with NgoMIV and AatII and a 4.7 kbp fragment containing the G418 expression cassette is gel purified and dephosphorylated. A 0.7 kbp region of DNA downstream of the KmGPD1F gene is amplified by PCR using primers identified as SEQ. ID. NO. 16 and SEQ. ID. NO. 17, again using *K. marxianus* genomic DNA as a template. The PCR product is gel purified, digested with NgoMIV and AatII, and ligated to the 4.7 kbp fragment of pVR29 to produce a plasmid designated as pBH159 (FIG. 2). Plasmid pBH159 contains, in order of transcription, the G418 expression cassette and the 0.7 kbp downstream flank of the KmGPD1F gene.

EXAMPLE 1C

Transformation of Strain CD853 (Ex. 1A) with Plasmids pBH158 and pBH159 (Ex. 1B, FIGS. 1 and 2) to Produce a Transformant (Strain CD1606) having an Exogenous LDH Gene, a Deletion of a Native PDC Gene, a Disrupted Native CYB2 Gene and a Deleted Native GPD1F Gene Plasmid pBH158 is digested with MluI and HindIII. These restriction enzymes cut the plasmid to produce a 2.6 kbp fragment that contains the 1.2 kbp upstream flank of the KmGPD1F gene and part of the G418 expression cassette. This fragment is isolated from an agarose gel. Plasmid pBH159 is digested with XhoI and NgoMIV. These restriction enzymes cut the plasmid to produce a 2.0 kbp fragment that contains a portion of the G418 expression cassette and the 0.7 kbp downstream flank of the KmGPD1F gene. This fragment is isolated from an agarose gel. The two isolated fragments together contain the entire G418 expression cassette with some duplication at the ends of the fragments.

Strain CD853 is grown overnight in YP+60 g/L glucose+ 0.2 M MES+1% ethanol, pH 6.5, and is electroporated simultaneously with the 2.6 kbp fragment from plasmid pBH158 and the 2.0 kbp fragment from pBH159. Transformants are selected on YP+20 g/L glucose+300 µg/mL G418 plates at 30° C. following 2 days of growth. 15 transformants are picked, restreaked to YP+20 g/L glucose+G418 plates and grown overnight. Only cells which have been cotransformed with both fragments and in which both fragments have become homologously integrated at the KmGPD1F locus will be resistant to G418.

Deletion of the KmGPD1F gene is verified by PCR using primers identified as SEQ. ID. NO. 18 and SEQ. ID. NO. 19. Seven transformants exhibit a single band of 3.4 kbp by PCR, indicating that the KmGPD1F gene is deleted in those transformants. One of these transformants is designated as strain CD1606.

EXAMPLE 2A

Construction of GPP Gene Deletion Vectors pBH160 (FIG. 3) and pBH161 (FIG. 4)

Plasmid pVR29 is digested with MluI and KpnI and a 5.1 kbp fragment containing the G418 gene cassette so obtained is gel purified and dephosphorylated. A 0.9 kbp region of DNA immediately upstream of the native GPP gene (KmHOR2 gene) is amplified by PCR using primers identified as SEQ. ID. NO. 20 and SEQ. ID. NO. 21, using *K. marxianus* genomic DNA as the template. The PCR product is gel purified, digested with MluI and KpnI, and ligated to the 5.1 kbp fragment from plasmid pVR29 to produce a plasmid designated as pBH160 (FIG. 3). Plasmid pBH160 contains, in order of transcription, the 0.9 kbp upstream flank of the KmHOR2 gene and the G418 expression cassette.

Plasmid pVR29 is digested with NgoMIV and SpeI and a 4.7 kbp fragment containing the G418 expression cassette is gel purified and dephosphorylated. A 0.8 kbp region of DNA immediately downstream of the KmHOR2 gene is amplified by PCR using primers identified as SEQ. ID. NO. 22 and SEQ. ID. NO. 23, using *K. marxianus* genomic DNA as the template. The PCR product is gel purified, digested with NgoMIV and SpeI, and ligated to the 4.7 kbp fragment of pVR29 to produce a plasmid designated as pBH161 (FIG. 4). Plasmid pBH161 contains, in order of transcription, the G418 expression cassette and the 0.8 kbp downstream flank of the KmHOR2 gene.

EXAMPLE 2B

Transformation of Strain CD853 (Ex. 1A) with Plasmids pBH160 and pBH161 (Ex. 2A, FIGS. 3 and 4) to Produce a Transformant (Strain CD1608) having an Exogenous LDH Gene, a Deletion of a Native PDC Gene, a Disrupted Native CYB2 Gene and a Deleted Native GPP Gene Plasmid pBH160 is digested with MluI and HindIII. These restriction enzymes cut the plasmid to produce a 2.3 kbp fragment that contains the 0.9 kbp upstream flank of the *K. marxianus* GPP (KmHOR2) gene and part of the G418 expression cassette. This fragment is isolated from an agarose gel. Plasmid pBH161 is digested with XhoI and NgoMIV. These restriction enzymes cut the plasmid to produce a 2.0 kbp fragment that contains the 0.8 kbp upstream flank of the KmHOR2 gene and part of the G418 expression cassette. This fragment is isolated from an agarose gel. The two isolated fragments together contain the entire G418 expression cassette with some duplication at the ends of the fragments.

Strain CD853 is grown overnight in YP+60 g/L glucose+ 0.2 M MES+1% ethanol, pH 6.5, and is then electroporated with both the 2.3 kbp fragment from plasmid pBH160 and the 2.0 kbp fragment from pBH161. Transformants are selected on YP+20 g/L glucose+300 µg/mL G418 plates at 30° C. following 2 days of growth. 15 transformants are restreaked to YP+20 g/L glucose+300 µg/mL G418 plates and grown overnight. All transformants grow on this medium. Only cells which have been cotransformed with both fragments and in which both fragments have become homologously integrated at the KmHOR2 locus will be resistant to G418.

Deletion of the KmHOR2 gene is verified by PCR using primers identified as SEQ. ID. NO. 20 and SEQ. ID. NO. 21. Three transformants yield a single 3.8 kbp band which is indicative of the deletion of the KmHOR2 gene. One of these transformants is designated strain CD1608.

EXAMPLE 3

Microaerobic Batch Culture Cultivation of Strains CD853 (Ex.1A), CD1606 (Ex. 1C) and CD1608 (Ex. 2B)

Strains CD853, CD1606 and CD1608 are separately cultivated under microaerobic conditions. Duplicate fermentations are performed in the cases of strains CD1606 and CD1608. In each case, a single-stage batch-culture reactor is used. The fermentation medium is a defined medium that includes ammonium sulphate, potassium dihydrogen phosphate and magnesium sulphate, trace elements, vitamins, defoaming agent, and about 90 g/L glucose. The pH of the medium is adjusted to about 3.0 by addition of potassium hydroxide. The medium is adjusted to 30° C. and inoculated with 1 mL of cells. The cells are cultured at 30° C. under agitation and aeration conditions that lead to an oxygen uptake rate of 5-6 mmol/L/hr. Oxygen uptake rate is determined according to methods described in WO 03/102,200.

Samples of the fermentation broth are removed periodically and assayed for lactate, acetate, glycerol and pyruvate.

Carbon dioxide production is measured by determining the carbon dioxide content of gasses vented from the reactor.

Strain CD853 (not an example of the invention) produces lactate at a rate of 0.85 g/L-hr through early stages of the fermentation, until the lactate titer is approximately 20 g/L. Lactate yield through that point is about 70%. After that, lactate production slows to about 0.76 g/L-hr and lactate yield drops slightly. Production for this strain is stopped after 86 hours, at which time the fermentation broth contains 11 g/L glucose. Lactate titer is 59 g/L. Overall lactate production rate is 0.65 g/L-hr, and overall yield to lactate is 70%. Yields to pyruvate, acetate, glycerol and carbon dioxide for strain CD853 are 0.6%, 0%, 5.1% and 14%, respectively. Yield to biomass is 6.4%.

Strain CD1606 produces lactate at a rate of 0.77-0.84 g/L-hr through early stages of the fermentation, until the lactate titer is approximately 20 g/L. Lactate yield through that point is about 72-80%. After that, lactate production slows to about 0.39-0.41 g/L-hr and lactate yield drops slightly. Production for this strain is stopped after 137 hours, at which time the fermentation broth contains 14-19 g/L glucose. Lactate titer is 43-45 g/L. Overall lactate production rate is 0.32-0.34 g/L-hr, and overall yield to lactate is 60-63%. Yields to pyruvate, acetate, glycerol and carbon dioxide for strain CD1606 are 0.1%, 0.5%, 0% and 26-29%, respectively. Yield to biomass is 7.9%. These results show that deletion of the native KmGPD1F gene is effective to disrupt the cell's capability to produce glycerol. Surprisingly, the deletion of this gene (and the resulting lack of glycerol production) has little or no effect on cell growth.

Strain CD1608 produces lactate at a rate of 0.66 g/L-hr through early stages of the fermentation, until the lactate titer is approximately 20 g/L. Lactate yield through that point is about 70-75%. After that, lactate production slows to about 0.37 g/L-hr and lactate yield drops slightly. Production for this strain is stopped after 137 hours, at which time the fermentation broth contains 19 g/L glucose. Lactate titer is 42 g/L. Overall lactate production rate is 0.31 g/L-hr, and overall yield to lactate is 59-60%. Yields to pyruvate, acetate, glycerol and carbon dioxide for strain CD1608 are 0.0-0.1%, 0.8%, 0% and 26-28%, respectively. Yield to biomass is 7.9-8.2%. These results show that deletion of the native KmHOR2 gene also is effective to disrupt the cell's capability to produce glycerol. Again, the deletion of this gene (and the resulting lack of glycerol production) has no effect on cell growth.

EXAMPLE 4A

Cloning of *I. orientalis* Native GPD1 Gene together with Upstream and Downstream Flanking Region Known glycerol-3-phosphate dehydrogenase genes from several yeast species (*S. cerevisiae, K. marxianus, Y. lipolytica, P. jadinii, D. hansenii* and *C. glabrata*) are aligned and regions which are highly conserved among the various genes are identified. Two sets of degenerate primers were designed in these regions of high homology. These sets are identified as SEQ. ID. NO. 24 and SEQ. ID. NO. 25, and SEQ. ID. NO. 26 and SEQ. ID. NO. 27, respectively. PCR is performed using the first set of primers and *I. orientalis* genomic DNA as the template, and a ~200 bp product is obtained as expected. PCR is again performed using the second set of primers and *I. orientalis* genomic DNA as the template, and a ~400 bp product is obtained as expected. The two PCR products are gel purified and sequenced using the same primers. Using the partial sequence so obtained, primers are designed for genome walking. Genome walking is performed using the BD Clontech Genome Walking Kit according to the manufacturer's instructions, using primary PCR primers identified as SEQ. ID. NO. 28 and SEQ. ID. NO. 29 and nested PCR primers identified as SEQ. ID. NO. 30 and SEQ. ID. NO. 31. Sequences obtained from both upstream and downstream genome walks are aligned and merged with the previously obtained partial sequence to construct the *I. orientalis* glycerol-3-phosphate dehydrogenase gene.

EXAMPLE 4B

Construction of a Plasmid (pMM28, FIG. 5) containing the KmCYB2 Gene Cassette between *K. thermotolerans* Direct Repeat Sequences The entire *K. marxianus* CYB2 (KmCYB2) gene cassette, including promoter and terminator regions, is PCR amplified from the genomic DNA of a wild-type *K. marxianus* strain designated as CD21, with introduction of BamHI and SalI restriction sites, by PCR using primers identified as SEQ. ID. NO. 32 and SEQ. ID. NO. 33. The PCR product is ligated to a commercial vector designated as pUC18 (from Invitrogen Corp., Carlsbad, Calif. USA) that is digested with BamHI and SalI. The resulting plasmid is designated as pMM25.

A 705 bp sequence identified as SEQ. ID. NO. 34 is PCR-amplified from the genomic DNA of *K. thermotolerans*, with introduction of SphI and SalI restriction sites, using primers identified as SEQ. ID. NO. 35 and SEQ. ID. NO. 36. This *K. thermotolerans* sequence does not encode for any active protein. Plasmid pMM25 is digested with SphI and SalI and the *K. thermotolerans* sequence is ligated to it upstream (5') to the KmCYB2 cassette to form a plasmid designated as pMM27.

An identical *K. thermotolerans* sequence is PCR-amplified with addition of BamHI and XmaI restriction sites, using primers identified as SEQ. ID. NO. 37 and SEQ. ID. NO. 38. Plasmid pMM27 is digested with BamHI and XmaI and the *K. thermotolerans* sequence is ligated to it downstream (3') from the KmCYB2 cassette to form a plasmid designated as pMM28 (FIG. 5). Plasmid pMM28 contains the KmCYB2 cassette flanked by *K. thermotolerans* direct repeat sequences, both oriented in the same direction.

EXAMPLE 4C

Construction of a Plasmid (pMI321, FIG. 7) Containing a Hygromycin Gene Cassette and a *L. helveticus* LDH Gene Cassette A 920 bp probe fragment of the *C. sonorensis* PGK1 gene is obtained from the genomic DNA of *C. sonorensis* in the same manner as described in Example 22 of WO 02/042471, using primers identified as SEQ. ID. NO. 39 and SEQ. ID. NO. 40. Genomic DNA is isolated from a growing *I. orientalis* strain and resuspended in 10 mM Tris-HCl+1 mM EDTA (pH 8) (TE). The *I. orientalis* genomic DNA is cut with HindIII and a Southern blot is prepared and hybridized using standard methods with the *C. sonorensis* PGK1 gene as a probe. Fragments of ~2 kb size are isolated from agarose gel and cloned into a HindIII-cut plasmid to generate a size-fractionated library, which is transformed into *E. coli*. Colony hybridization of the size-fractionated library with the PGK1 probe results in isolation of a plasmid containing a HindIII fragment with most of the *I. orientalis* PGK1 (IoPGK1) protein coding sequences but no promoter sequence, as verified by sequencing.

Genomic fragments containing the IoPGK1 promoter region are obtained with ligation-mediated PCR amplification (Mueller, P. R. and Wold, B. 1989, "In vivo footprinting of a muscle specific enhancer by ligation mediated PCR." *Science* 246:780-786). A mixture of a linker identified as SEQ. ID. NO. 41 and a linker identified as SEQ. ID. NO. 42 is ligated to HaeIII-digested *I. orientalis* genomic DNA with T4 DNA ligase (New England BioLabs). Samples of the ligation mixtures are used as templates for 50 1 PCR reactions containing 0.1 M of a primer identified as SEQ. ID. NO. 43 and 1 M of a primer identified as SEQ. ID. NO. 44. The reaction mixture is heated at 94° C. for 3 minutes after 2 U of Dynazyme EXT is added. The reactions are cycled 30 times as follows: 1 minute at 94° C., 2 minutes at 68° C. and 2 minutes at 72° C., with a final extension of 10 minutes at 72° C. A diluted sample of this first PCR-amplification is used as the template in a nested PCR reaction (50 1) containing 0.05 M of a primer identified as SEQ. ID. NO. 45 and 0.5 M of a primer identified as SEQ. ID. NO. 46. The reaction mixture is heated at 94° C. for 3 minutes after 2 U of Dynazyme EXT is added. The reactions are then cycled 30 times as follows: 1 minute at 94° C., 2 minutes at 67° C. and 2 minutes at 72° C., with a final extension of 10 minutes at 72° C.

A ~600 bp PCR fragment is isolated and sequenced. Nested primers identified as SEQ. ID. NO. 47 and SEQ. ID. NO. 48 are designed and used in a ligation-mediated PCR amplification together with oligonucleotides identified as SEQ. ID. NO. 49 and SEQ. ID. NO. 50 similarly as above, except that SspI-digested *I. orientalis* DNA is used and the PCR is carried out using an annealing temperature of 65° C.

The *I. orientalis* PGK1 promoter region is PCR amplified using primers identified as SEQ. ID. NO. 51 and SEQ. ID. NO. 52 and the *I. orientalis* genomic DNA as the template. The fragment is filled in using the Klenow enzyme and then cut with XbaI. A 633 bp fragment is gel isolated and ligated to a 4428 bp fragment obtained by digesting a plasmid designated as pMI270 (described in FIG. 4 of WO 03/049525) with XhoI, filling the fragment in using the Klenow enzyme and 0.1 mM dNTP, and digesting with XbaI. Plasmid pMI270 contains the *E. coli* hygromycin gene linked to a *C. sonorensis* PGK1 promoter and a *S. cerevisiae* GAL10 terminator. The resulting plasmid is designated pMI318 (FIG. 6). Plasmid pMI318 contains the *E. coli* hygromycin gene under the control of the *I. orientalis* PGK1 promoter and the *S. cerevisiae* GAL10 terminator.

The I. orientalis PGK1 promoter is PCR amplified using primers identified as SEQ. ID. NO. 53 and SEQ. ID. NO. 54 and I. orientalis genomic DNA as the template. The fragment is filled in using the Klenow enzyme and 0.1 mM dNTP, and then cut with NcoI. A 633 bp fragment is gel isolated. Plasmid pVR1 (described in WO 03/102152 FIG. 7) contains the *L. helveticus* LDH gene under the control of the *S. cerevisiae* TEF1 promoter and the *S. cerevisiae* CYC1 terminator. Plasmid pVR1 is digested with XhoI, filled in using the Klenow enzyme, and cut with NcoI. A 7386 bp fragment from plasmid pVR1 is ligated to the 633 bp IoPGK1 promoter fragment. The resulting plasmid is designated pMI320. Plasmid pMI320 contains the *L. helveticus* LDH gene under the control of the IoPGK1 promoter and *S. cerevisiae* CYC1 terminator.

Plasmids pMI318 and pMI320 are digested with ApaI and NotI. A 5008 bp fragment from plasmid pMI318 is ligated to a 1995 bp fragment from plasmid pMI320 to form plasmid pMI321 (FIG. 7).

The hygromycin gene (and its terminator) is positioned on plasmid pMI321 between two copies of the IoPGK1 promoter, which serve as direct repeat sequences.

EXAMPLE 4D

Construction of a Plasmid (pMI355, FIG. 8) having the *E. coli* Hygromycin Gene Cassette, the *L. helveticus* LDH Gene Cassette, and the IoPDC1A 5' Flanking Region A genomic library of the wild-type *I. orientalis* strain ATCC PTA-6658 is constructed into the SuperCos1 (Stratagene) cosmid vector according to instructions provided by the manufacturer. PDC-like sequences are amplified by PCR from the genomic DNA of the strain with primers designated as SEQ. ID. NO. 55 and SEQ. ID. NO. 56. A 700 bp fragment of a PDC gene is amplified. The genomic library is screened using hybridization techniques with labeled PCR fragments as the probe as described in WO 03/049525 and cosmid clones containing the PDC gene are isolated and sequenced. The *I. orientalis* PDC1A 5' region from 1000 bp to 167 bp upstream of the start of the open reading frame is PCR amplified using primers identified as SEQ. ID. NO. 57 and SEQ. ID. NO. 58 and the *I. orientalis* PDC1A cosmid DNA as the template. The fragment is cut with SalI and SacI. An 836 bp fragment is gel isolated and ligated to a 6992 bp fragment obtained by digesting plasmid pMI321 (FIG. 7, Example 4C) with SalI and SacI. The resulting plasmid is named pMI355 (FIG. 8).

EXAMPLE 4E

Construction of Plasmids (pMI356 and pMI357 (FIG. 9)) containing the IoPDC1A 5' Flanking Region, the *E. coli* Hygromycin Gene Cassette, the *L. helveticus* LDH Gene Cassette, and an IoPDC1A 3' Flanking Region The *I. orientalis* PDC1A 3' region corresponding to sequences from 524 bp upstream to 217 bp downstream of the PDC translation stop codon is PCR amplified using primers identified as SEQ. ID. NO. 59 and SEQ. ID. NO. 60 and the *I. orientalis* PDC1A cosmid DNA (Example 4D) as the template. The fragment is cut with ApaI and SmaI. A 630 bp fragment is gel isolated and ligated to a 7809 bp fragment obtained by digesting plasmid pMI355 (FIG. 8, Ex. 4D) with ApaI and SmaI. The resulting plasmid is named pMI357 (FIG. 9). It contains the hygromycin and LDH cassettes from plasmid pMI355 between the 5' flank and a portion of the 3' flank of the IoPDC1A gene.

Plasmid pMI356 is constructed in the same way, except a different section of the *I. orientalis* PDC1A 3' region is used.

EXAMPLE 4F

Construction of Plasmid pMI433 (FIG. 10) containing the IoPDC1A 5' Flanking Region, a ScMEL5 Gene Cassette, the *L. helveticus* LDH Gene Cassette and the IoPDC1A 3' Flanking Region The *I. orientalis* PGK1 promoter is PCR amplified using primers identified as SEQ. ID. NO. 61 and SEQ. ID. NO. 62 and the *I. orientalis* genomic DNA as the template. The fragment is filled in using the Klenow enzyme and 0.1 mm dNTP, and then cut with SphI. A 669 bp fragment is gel isolated. A plasmid designated as pMI233 (described in FIG. 23C of WO 03/049525) is cut with XhoI. The fragment is filled in with the Klenow enzyme and cut with SphI. The 4534 bp and the 669 bp fragments are ligated and the resulting plasmid is named pMI319. Plasmid pMI319 contains the *S. cerevisiae* MEL5 (ScMEL5) gene and the IoPGK1 promoter region.

Plasmid pMI319 plasmid is cut with ApaI, made blunt ended with T4 polymerase, and cut with NotI. A 2317 bp fragment is gel isolated. It is ligated to a 6498 bp fragment obtained by digesting plasmid pMI357 (Example 4E) with SalI, making it blunt ended with the Klenow enzyme and then cutting with NotI. The resulting plasmid contains the ScMEL5 gene (with its native terminator) in place of the hygromycin gene of plasmid pMI357. The resulting plasmid is designated pMI433 (FIG. 10).

EXAMPLE 4G

Construction of Plasmids pMI449 (FIG. 11) and pMI454 (FIG. 12) Containing *I. orientalis* CYB2 5' Flanking Region, ScMEL5 Gene Cassette between *K. thermotolerans* Direct Repeat Sequences and *I. orientalis* CYB2 3' Flanking Region Plasmid pMM28 (FIG. 5, Ex. 4B) is digested with BamHI, filled in with the Klenow enzyme, and digested with SalI. The 4077 bp fragment so obtained is ligated to a 2317 bp NotI (filled in with Klenow enzyme)-SalI fragment of pMI433 (FIG. 10, Ex. 4F). The resulting plasmid is designated pMI445.

The 3' flanking region of the *I. orientalis* L-lactate:ferricytochrome c oxidoreductase (IoCYB2A) gene (corresponding to sequences from 90 to 676 bp downstream of the the start of the predicted open reading frame) is amplified by PCR using primers identified as SEQ. ID. NO. 63 and SEQ. ID. NO. 64, using a CYB2-2 cosmid clone as a template. The PCR product is digested with SacI and SmaI and the 607 bp fragment is ligated to the 6386 bp SacI-SmaI fragment of plasmid pMI445. The resulting plasmid is designated pMI448.

The IoCYB2A 5' flanking region (corresponding to sequences from 913 to 487 bp upstream of the start of the predicted open reading frame) is amplified by PCR using primers identified as SEQ. ID. NO. 65 and SEQ. ID. NO. 66, again using the CYB2-2 cosmid clone as a template. The PCR product is digested with SphI and the 454 bp fragment is ligated to the 6993 bp SphI fragment obtained by partially digesting pMI448. The resulting plasmid is designated pMI449 (FIG. 11).

The IoCYB2A 5' flanking region (corresponding to sequences from 466 to 7 bp upstream of the predicted open reading frame) is amplified by PCR using primers identified as SEQ. ID. NO. 67 and SEQ. ID. NO. 68, once again using the CYB2-2 cosmid clone as the template. The PCR product is digested with SphI and the 493 bp fragment is ligated to the 6993 bp SphI fragment obtained by partially digesting plasmid pMI448. The resulting plasmid is designated pMI453.

The IoCYB2A 3' flanking region (corresponding to sequences from 402 bp upstream to 77 bp downstream of the predicted stop codon) is amplified by PCR using primers identified as SEQ. ID. NO. 69 and SEQ. ID. NO. 70, using the CYB2-2 cosmid as a template. The PCR product is digested with ApaI and SmaI and the 506 bp fragment is ligated to the 6886 bp ApaI-SmaI fragment of plasmid pMI453. The resulting plasmid is designated pMI454 (FIG. 12).

EXAMPLE 4H

Construction of a Plasmid (pBH165, FIG. 13) Containing an Upstream Fragment of the IoGPD1 Gene, a First *K. thermotolerans* Direct Repeat Section, a MEL5 Gene Cassette, a Second *K. thermotolerans* Direct Repeat Section, and a Downstream Fragment of the IoGPD1 Gene Plasmid pMI449 is digested with NdeI and SbfI to excise the 5' CYB2A flanking homology. A 6.8 kbp fragment is gel purified and dephosphorylated. A 302 bp fragment of the IoGPD1 gene from Example 4A (corresponding to base pairs 1-302 from the start codon of the gene) is amplified by PCR using primers identified as SEQ. ID. NO. 71 and SEQ. ID. NO. 72. The PCR product is gel purified, digested with NdeI and SbfI, and ligated to the 6.8 kbp fragment from plasmid pMI449 to produce plasmid pBH164. Plasmid pBH164 is then digested with XmaI and EcoRI to excise the 3' CYB2A flanking homology. A 6.5 kbp fragment is gel purified and dephosphorylated. A 346 bp fragment of the IoGPD1 gene from Example 4A (corresponding to base pairs 322-668 from the start codon) is amplified by PCR using primers identified as SEQ. ID. NO. 73 and SEQ. ID. NO. 74. The PCR product is gel purified, digested with XmaI and EcoRI, and ligated to the 6.5 kbp fragment obtained from pBH164 to produce pBH165 (FIG. 13).

Plasmid pBH165 contains, in order of transcription, the 302 bp fragment of the IoGPD1 gene, a first *K. thermotolerans* direct repeat section, a MEL5 gene cassette, a second *K. thermotolerans* direct repeat section, and the 346 bp fragment of the IoGPD1 gene. It is designed for insertion at the locus of the native IoGPD1 gene (with disruption of the gene), followed by a loop-out of the MEL5 gene cassette.

EXAMPLE 4I

Generation of an *I. orientalis* Mutant (CD1184) with Deleted IoPDC1A and IoPDC1B Genes and Integrated LhLDH Gene in one Step by Transforming Wild-Type *I. orientalis* Strain with Plasmid pMI356 (Ex. 4F)

Wild-type *I. orientalis* strain ATCC PTA-6658 is transformed with plasmid pMI356 using standard methods. Transformed strains that grow on hygromycin plates are cultured. A transformant that does not produce ethanol is selected for Southern analysis, which confirms the deletion of both IoPDC1A alleles and insertion of at least one copy of the LhLDH gene. This strain is designated CD1184.

EXAMPLE 4J

Generation of *I. orientalis* Mutant Strain (CD1496) by Successively Transforming Strain CD1184 (Ex. 4I) with Plasmids pMI449 (Ex. 4G, FIG. 11) and pMI454 (Ex. 4G, FIG. 12), Followed by Mutagenesis.

Strain CD1184 is transformed with plasmid pMI449 using the lithium acetate method and transformants (blue colonies) are selected based on melibiase activity on YPD X--gal plates. The replacement of the IoCYB2A gene of strain CD1184 is confirmed by colony PCR and Southern analysis in some of the transformants. The MEL5 marker is looped out from one of those transformants via a homologous recombination event through the K. thermotolerans repeat sequences, as confirmed by Southern analysis. The second CYB2A allele is then deleted from this transformant using plasmid pMI454. Transformants are analyzed by colony PCR for the absence of a 1000 bp CYB2A-specific PCR product. The MEL5 marker from plasmid pMI454 is looped out of a transformant having a deletion of the second CYB2A allele via recombination as before. This transformant is designated strain CD1436. Strain CD1436 has a deletion of both PDC1 genes (with replacement by a functional L-LDH gene cassette), and a deletion of each of its two native IoCYB2 genes.

Strain CD1436 is subjected to EMS mutagenesis using the conditions set forth in Example 1A, except the exposure conditions are 8 μL for 1 hour. Mutagenized cells are allowed to recover for 6 hours in 200 μL of YP+20 g/L glucose media and then plated onto PDA+35 g/L lactic acid plates and incubated for one week at 30° C. A strain that produces more lactate and less glycerol than strain CD1436 is designated as strain CD1496.

EXAMPLE 4K

Transformation of Strains CD1184 (Ex. 41) and CD 1496 (Ex. 4J) with Plasmid pBH165 (Ex. 4H, FIG. 13), followed by Loop-Out of the Selection Marker to Produce Transformant Strains CD1667 and CD1671, Respectively, which have a Single GPD1 Allele Deleted Strain CD1184 is grown and transformed with 5 g of the 4.4 kbp fragment obtained by digesting plasmid pBH165 with NdeI and EcoRI. Transformants are selected on yeast nitrogen base (YNB)+2% melibiose plates overlaid with x-α-gal (-4-chloro-3-indolyl-aD-galactopyranoside). Blue-colored transformants are visible after ~4 days of growth at 30° C. Eight transformants are picked and plated for single colonies on YP+20 g/L glucose plates containing x-α-gal. A single blue colony for each transformant is picked and restreaked to YP+20 g/L glucose plates. Genomic DNA is isolated from the transformants. Disruption of one allele of the IoGPD1 gene is verified by PCR using primers identified as SEQ. ID. NO. 75 and SEQ. ID. NO. 76. Five transformants exhibit the expected ~2 kb product. One of those transformants is designated as strain CD1655. Disruption of one copy of the native IoGPD1 gene is further verified by PCR using primers designated as SEQ. ID. NO. 77 and SEQ. ID. NO. 78.

Strain CD1655 is grown for several rounds in YP+100g/L glucose at 30° C. A dilution series is plated onto YP+20 g/L plates overlaid with x- -gal, and grown overnight at 30° C. A white colony (indicative of the loop-out of the MEL 5 marker cassette) is selected and restreaked to YP+20 g/L glucose+x- -gal plates. A white colony is selected. Disruption of one allele of the native IoGPD1 gene is verified by PCR using primers identified as SEQ. ID. NO. 69 and SEQ. ID. NO. 80. This transformant is designated as strain CD1667.

Strain CD1496 is transformed in the same manner. A transformant exhibiting the expected ~2kbp band on PCR is designated as strain CD1657. Disruption of one allele of the native IoGPD1 gene is verified by PCR as described for strain CD1655. Strain CD1657 is further grown for several rounds, and a colony showing a deletion of the MEL5 marker gene cassette is selected and designated as strain CD1671. Disruption of one allele of the native IoGPD1 gene is verified by PCR as before.

EXAMPLE 4L

Transformation of Strains CD1667 (Ex. 4K) and CD1671 (Ex. 4K) with Plasmid pBH165 (Ex. 4H, FIG. 13) to Produce Transformant Strains CD1688 and CD1690, respectively, with both IoGPD1 Alleles Deleted Strain CD1667 is transformed with 5 g of a 4.4 kbp fragment obtained by digesting plasmid pBH165 with NdeI and EcoRI. Transformants are selected on YNB +2% melibiose plates overlaid with x-α-gal. Blue-colored transformants are visible after ~4 days of growth at 30° C. Ten transformants are picked and plated for single colonies on YP+20 g/L glucose plates containing x-α-gal. A single blue colony for each transformant is picked and restreaked to YP+20 g/L glucose. Genomic DNA is isolated from the transformants. Disruption of the second allele of the IoGPD1 gene is verified in three transformants by PCR using primers identified as SEQ. ID. NO 81 and SEQ. ID. NO. 82. One of these transformants is designated as strain CD1688.

Strain CD1671 is transformed in the same manner. PCR shows that the second allele of the IoGPD1 gene is disrupted in one transformant, which is designated strain CD1690.

EXAMPLE 5

Microaerobic Batch Culture Cultivation of Strains CD1184 (Ex. 41) and CD1688 (Ex. 4L) at an OUR of 5.5-5.6.

A single-stage batch-culture reactor containing a defined medium that includes ammonium sulphate, potassium dihydrogen phosphate and magnesium sulphate, trace elements, vitamins, defoaming agent, and about 50 g/L glucose is inoculated with 1 mL strain CD1688. The pH of the medium is adjusted to about 3.5 prior to adding the cells. The pH of the culture is allowed to drop to 3.0 as cells grow and begin to produce lactic acid. Afterward, pH is maintained at about 3.0 by addition of potassium hydroxide. Glucose is fed to the fermentation at about 1-2 g/L/hr until a total of 136.1 g/L glucose has been added. The cells are cultured at 30° C. under aeration conditions that lead to an oxygen uptake rate of about 5.5-5.6 mmol/L/hr.

Strain CD1688 produces lactate at a rate of 1.02 g/L-hr until the lactate titer is approximately 70 g/L. Lactate yield through that point is about 74%. Production for this strain is stopped after 77 hours, at which time the fermentation broth contains 15.3 g/L glucose. Overall lactate production rate is 1.06 g/L-hr, and overall yield to lactate is 70%. Yields to pyruvate, glycerol and carbon dioxide for strain CD1688 are 1.9%, 0% and 23.7%, respectively. Yield to biomass is 3.5%.

For comparison, strain CD1184 (not an example of the invention) is cultured under similar conditions. Strain CD1184 produces lactate at a rate of 1.24 g/L-hr until the lactate titer is approximately 70 g/L. Lactate yield through that point is about 74%. Production for this strain is stopped after 77 hours, at which time the fermentation broth contains 15.3 g/L glucose. Overall lactate production rate is 1.06 g/L-hr, and overall yield to lactate is 70%. Yields to pyruvate, glycerol and carbon dioxide for strain CD1184 are 2.1%, 9.3% and 15.9%, respectively. Yield to biomass is 3.2%.

These results show that under these fermentation conditions, deletion of the native IoGPD1 genes prevents the cell from producing measurable quantities of glycerol. As before, the deletion of this gene (and the resulting lack of glycerol production) has little or no effect on cell growth.

EXAMPLE 6

Microaerobic Batch Culture Cultivation of Strains CD1184 (Ex. 41) and CD1688 (Ex. 4L) at an OUR of 9.9-10

Strains CD1688 and CD1184 are separately cultivated in the general manner described in Example 5, except aeration conditions are selected to lead to an oxygen uptake rate of 9.9-10.0 mmol/L/hr, and no glucose is fed to the system during the cultivation. Yeast hulls are added to the cultivation of strain CD1688.

Under these conditions, strain CD1184 produces lactate at a rate of 1.87 g/L-hr until the lactate titer is approximately 70 g/L. Lactate yield through that point is about 73%. Production for this strain is stopped after 67.5 hours, at which time the glucose concentration in the fermentation broth has been reduced from 60 g/L to 2.1 g/L. Overall lactate production rate is 1.43 g/L-hr, and overall yield to lactate is 70%. Yields to pyruvate, glycerol and carbon dioxide for strain CD1184 are 2.1%, 5.7% and 21.5%, respectively. Yield to biomass is 4.4%.

Strain CD1688 produces lactate at a rate of 1.68 g/L-hr until the lactate titer is approximately 70 g/L. Lactate yield through that point is about 80%. Production for this strain is stopped after 78 hours, at which time the glucose concentration in the fermentation broth has been reduced from 53.5 g/L to 4.8 g/L. Overall lactate production rate is 1.26 g/L-hr, and overall yield to lactate is 77%. Yields to pyruvate, glycerol and carbon dioxide for strain CD1688 are 1.2%, 0% and 23.2%, respectively. Yield to biomass is 5.95%. As before, these results show that under these fermentation conditions, deletion of the native IoGPD1 genes prevents the cell from producing measurable quantities of glycerol and that the deletion of this gene (and the resulting lack of glycerol production) has no effect on cell growth. In addition, deletion of IoGPD1 improves overall lactate yield.

EXAMPLE 7

Microaerobic Batch Culture Cultivations of Strain CD1690 (Ex. 4L) at an OUR of 5-6

Strain CD1690 is cultivated in the general manner described in Example 5, except aeration conditions are selected to lead to an oxygen uptake rate of 5.75 mmol/L/hr, and the fermentation medium is YP+70 g/L glucose.

Under these conditions, strain CD1690 produces lactate at a rate of 0.66 g/L-hr until the lactate titer is approximately 70 g/L. Lactate yield through that point is about 78%. Production for this strain is stopped after 121 hours, at which time the glucose concentration in the fermentation broth has been reduced to 23.8 g/L (out of 127.9 g/L provided to the cultivation). Overall lactate production rate is 0.61 g/L-hr, and overall yield to lactate is 77%. Yields to pyruvate, glycerol and carbon dioxide are 0%, 0% and 31.1%, respectively. Yield to biomass is 2.4%. Once again, these results show that under these fermentation conditions, deletion of both of the native IoGPD1 alleles prevents the cell from producing measurable quantities of glycerol, and has little or no effect on cell growth.

Strain CD1690 is cultivated twice more in the general manner described in Example 5 (using the defined medium described there), except the OUR is 5.2 mmol/L/hr and glycerol is added to the fermentation broth. In the first run, 0.1 g/L glycerol is added and 1.0 g/L glycerol is added in the second run.

When 0.1 g/L glycerol are added, strain CD 1690 produces lactate at a rate of 0.74 g/L-hr until the lactate titer is approximately 70 g/L. Lactate yield through that point is about 78%. Production for this strain is stopped after 121 hours, at which time the glucose concentration in the fermentation broth has been reduced to 10.2 g/(out of 117.8 g/L provided to the cultivation). Overall lactate production rate is 0.68 g/L-hr, and overall yield to lactate is 76%. Yields to pyruvate, glycerol and carbon dioxide are 0.2%, 0% and 25.3%, respectively. Yield to biomass is 4.1%.

Very similar results are obtained when 1.0 g/L glycerol are added.

These results unexpectedly show that the addition of glycerol to the fermentation medium has little or no effect on the ability of these transformants to grow and produce lactate, despite the disruption of the cells' native ability to produce glycerol.

EXAMPLE 8A

Construction of a Plasmid (pTMC61 (FIG. 14)) Containing the IoGPD1 5' Flanking Region, the *E. coli* Hygromycin Gene Cassette between Direct Repeats, and the IoGPD1 3' Flanking Region The hygromycin gene cassette is PCR amplified using primers identified as SEQ. ID. NO. 83 and SEQ. ID. NO. 84, with plasmid pMI356 (Ex. 4E, see FIG. 9) as the template. PCR conditions are 95° C. for 5 minutes (once), 30 cycles of 95° C. (30 seconds), 56° C. (30 seconds) and 72° C. (2 minutes), followed by one cycle of 72° C. for 10 minutes. The resulting PCR product is digested with SpeI and SalI, and ligated onto plasmid pBH165 (Ex. 4H, FIG. 13), which has been similarly digested, to produce plasmid pTMC61 (FIG. 14).

EXAMPLE 8B

Transformation of Selected Wild-Type *I. orientalis* Strain with Plasmid pBH165 (Ex. 4H, FIG. 13), Followed by Loop-Out of the Selection Marker to Produce Transformant Strain CD2624, which has a Single GPD1 Allele Deleted Wild-type *I. orientalis* strain ATCC PTA-6658 is grown for many generations in continuous culture in a medium containing a low concentration of glucose and a high concentration of lactic acid. A cell that grows well under these conditions is isolated and designated as strain CD1822. Strain CD1822 produces ethanol and glycerol when cultivated in a medium containing glucose as the carbon source. Strain CD1822 is grown and transformed with plasmid pBH165 in the same manner as described in Example 4K. Transformants are selected on yeast nitrogen base (YNB)+ 2% melibiose plates overlaid with x-α-gal (5-bromo-4-chloro-3-indolyl-a-D-galactopyranoside), as described in Example 4K, with a blue colony being picked and restreaked to YP+20 g/L glucose plates. Genomic DNA is isolated from the transformant, and analyzed for integration of the deletion construct by two sets of PCR reactions. The first of these used primers designated as SEQ. ID. NO. 85 and SEQ. ID. NO. 86, and the second of these was performed with primers designated as SEQ. ID. NO. 87 and SEQ. ID. NO. 88. These produced PCR products of 2.0 kbp and 1.4 kbp, respectively, indicating that one of the GPD1 alleles has been disrupted. A third PCR reaction is performed, using primers designated as SEQ. ID. NO. 85 and SEQ. ID. NO. 88; this produces a 0.8 kbp product indicating that an undisrupted GPD1 allele is still present in the transformant. The transformant is designated as strain CD2624.

EXAMPLE 8C

Transformation of Strain CD2624 (Ex. 8B) with Plasmid pTMC61 (Ex. 8A, FIG. 14) to Produce Transformant Strains CD2627, having both IoGPD1 Alleles Deleted PCR is performed using primers identified as SEQ. ID. NO. 89 and SEQ. ID. NO. 90, with plasmid pTMC61 as the template. A 4.1 kbp fragment is obtained, and is used to transform strain CD2624. Transformants are selected on YPD+300 g/ml hygromycin. Genomic DNA is isolated from 100 of the transformants, and used as a template in three sets of PCR reactions. The first uses primers identified as SEQ. ID. NO. 91 and SEQ. ID. NO. 88, and produces a 1.5 kbp product in 30 of the transformants. A second PCR reaction is conducted on genomic DNA from those 30 transformants, using primers identified as SEQ. ID. NO. 85 and SEQ. ID. NO. 92. Ten strains exhibited the expected 2.5 kbp product. Genomic DNA from those ten strains are then analysed using primers identified as SEQ. ID. NO. 85 and SEQ. ID. NO. 88. Two strains that do not product a 0.8 kbp fragment have both GPD1 alleles disrupted. These are tested for grown on YNB+2.0% melibiose plates. One strain is able to grow, and is designated as strain CD2627.

EXAMPLE 8D

Microaerobic Cultivation of Strain CD1822, Strain CD2624 (Example 8B) and Strain CD2627 (Example 8C)

Strains CD1822, CD2624 and CD2627 are cultivated in duplicate microaerobic shake flask fermentations. The strains are grown overnight in 25 mL a defined medium containing ~100g/mL glucose, at 30° C. and 250 rpm stirring in 250 mL baffled flasks. The defined medium is as described in Peter M. Bruinenberg, Johannes P. Van Dijken and W. Alexander Schefferes, 1983, An Enzymatic Analysis of NADPH Production and Consumption in *Candida utilis*, *J. General Microbiology* vol.129, pp.965-971, except for the presence of additional glucose as indicated and an increase in nicotinic acid to 5 mg/L.

The resulting cultures are used to inoculate 50 mL of the defined medium containing 100 g/L glucose in 250 mL baffled flasks to an $OD_{600}$ of 0.2. These flasks are then incubated at 100 rpm for 22 hours at 30° C. The medium is then analyzed by HPLC for glucose, glycerol and ethanol. Yield to biomass is also determined.

Strain CD1822 consumes all of the glucose during the 22 hour cultiviation, producing 6.0 g/kg of glycerol, 34.54 g/kg of ethanol and biomass to an $OD_{600}$ of 14.8.

Strain CD2624, which has a disruption of one GPD1 allele, consumes all of the glucose, producing 5.88 g/kg of glycerol and 35.25 g/kg of ethanol. Biomass is produced to an $OD_{600}$ of 14.5.

Strain CD2627, which has a disruption of both GPD1 alleles, consumes all but 12.39 g/kg of the glucose during 22 hours. Glycerol production is 0.34 g/kg. Ethanol production is 23.06 g/kg and biomass is produced to an $OD_{600}$ of 11.5. These results indicate that disruption of the GPD1 alleles in *I. orientalis* results in a small reduction in glucose consumption rates, and a small reduction in ethanol production and biomass production, under these conditions. However, strain CD2627 grows well and produces ethanol well, with minimal glycerol production. The results further indicate that the ability of the GPD1 deletants to grow and produce is not dependent on the disruption of PDC activity or the addition of a pathway from pyruvate to lactate.

The invention claimed is:

1. A yeast cell of species *Issatchenkia orientalis* that is genetically modified to produce lactate, said yeast cell further having a deletion or disruption of (i) a native gene encoding a glycerol-3-phosphate dehydrogenase and/or a native gene encoding a glycerol-3-phosphatase, and (ii) a pyruvate decarboxylase gene, wherein the yeast cell contains an exogenous lactate dehydrogenase gene.

2. The yeast cell of claim 1 wherein the cell includes a deletion or disruption of at least one native glycerol-3-phosphate dehydrogenase gene.

3. The yeast cell of claim 1 wherein the cell includes a deletion or disruption of at least one native glycerol-3-phosphatase gene.

4. The yeast cell of claim 3 wherein the cell includes a deletion or disruption of at least one native glycerol-3-phosphase dehydrogenase gene and of at least one native glycerol-3-phosphatase gene.

5. The yeast cell of claim 1, wherein the exogenous lactate dehydrogenase gene is obtained from an organism selected from the group consisting of *L. helveticus, L. casei, B. megaterium*, and *P. acidilactici*.

6. The yeast cell of claim 1, wherein the strain is capable of producing at least 70 gram/liter lactate.

* * * * *

SEQUENCE LISTING

```
<160> NUMBER OF SEQ ID NOS: 92

<210> SEQ ID NO 1
<211> LENGTH: 415
<212> TYPE: PRT
<213> ORGANISM: Issatchenkia orientalis
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
```

<400> SEQUENCE: 1

```
Met Phe Leu Ile Ser Lys Ser Leu His Phe Thr Arg Ser Xaa Ser Asn
1               5                   10                  15

Thr Ile Lys Thr Leu Asn Arg Ser Asn Ile Lys Met Val Ser Pro Ala
            20                  25                  30

Glu Arg Leu Ser Thr Ile Ala Ser Thr Ile Lys Pro Asn Arg Lys Asp
        35                  40                  45

Ser Thr Ser Leu Gln Pro Glu Asp Tyr Pro Glu His Pro Phe Lys Val
    50                  55                  60

Thr Val Val Gly Ser Gly Asn Trp Gly Cys Thr Ile Ala Lys Val Ile
65                  70                  75                  80

Ala Glu Asn Thr Val Glu Arg Pro Arg Gln Phe Gln Arg Asp Val Asn
                85                  90                  95

Met Trp Val Tyr Glu Glu Leu Ile Glu Gly Lys Leu Thr Glu Ile
                100                 105                 110

Ile Asn Thr Lys His Glu Asn Val Lys Tyr Leu Pro Gly Ile Lys Leu
            115                 120                 125

Pro Val Asn Val Val Ala Val Pro Asp Ile Val Glu Ala Cys Ala Gly
        130                 135                 140

Ser Asp Leu Ile Val Phe Asn Ile Pro His Gln Phe Leu Pro Arg Ile
145                 150                 155                 160

Xaa Ser Gln Leu Lys Gly Lys Val Asn Pro Lys Ala Arg Ala Ile Ser
                165                 170                 175

Cys Leu Lys Gly Leu Asp Val Asn Pro Asn Gly Cys Lys Leu Leu Ser
            180                 185                 190

Thr Val Ile Thr Glu Glu Leu Gly Ile Tyr Cys Gly Ala Leu Ser Gly
            195                 200                 205

Ala Asn Leu Ala Pro Glu Val Ala Gln Cys Lys Trp Ser Glu Thr Thr
210                 215                 220

Val Ala Tyr Thr Ile Pro Asp Asp Phe Arg Gly Lys Gly Lys Asp Ile
225                 230                 235                 240

Asp His Gln Ile Leu Lys Ser Leu Phe His Arg Pro Tyr Phe His Val
            245                 250                 255

Arg Val Ile Ser Asp Val Ala Gly Ile Ser Ile Ala Gly Ala Leu Xaa
            260                 265                 270

Asn Val Ala Met Ala Ala Gly Phe Val Glu Gly Leu Gly Xaa Gly
            275                 280                 285

Asp Asn Ala Lys Ala Ala Val Met Arg Ile Gly Leu Val Glu Thr Ile
        290                 295                 300

Gln Phe Ala Lys Thr Phe Phe Asp Gly Cys His Ala Ala Thr Phe Thr
305                 310                 315                 320

His Glu Ser Ala Gly Val Ala Asp Leu Ile Thr Thr Cys Ala Gly Gly
                325                 330                 335

Arg Asn Val Arg Val Gly Arg Tyr Met Ala Xaa His Ser Val Ser Ala
            340                 345                 350

Thr Glu Ala Glu Glu Lys Leu Leu Asn Gly Gln Ser Cys Gln Gly Ile
        355                 360                 365

His Thr Thr Arg Glu Val Tyr Glu Phe Leu Ser Asn Met Gly Arg Thr
    370                 375                 380

Asp Glu Phe Pro Leu Phe Thr Thr Thr Tyr Arg Ile Ile Tyr Glu Asn
385                 390                 395                 400

Phe Pro Ile Glu Lys Leu Pro Glu Cys Leu Glu Pro Val Glu Asp
```

```
                      405                 410                 415

<210> SEQ ID NO 2
<211> LENGTH: 434
<212> TYPE: PRT
<213> ORGANISM: Kluyveromyces marxianus

<400> SEQUENCE: 2

Met Ile Gln Phe Gly Arg Ser Phe Cys Tyr Asn Ser Ile Val Lys Ser
1               5                   10                  15

Phe Gln Ile Arg Lys Ser Ile Thr Arg Phe Arg Leu Thr Asp Ile Tyr
                20                  25                  30

Thr Asn Arg Val Thr Ile Asn Thr Arg Asn Ile Ser Asn Met Ser
            35                  40                  45

Pro Ala Ser Asp Arg Leu Lys Gln Thr Ser Ser Ile Leu Ser Lys Ser
        50                  55                  60

Val Glu Pro Lys Ala Asp Ser Pro Phe Lys Val Thr Val Ile Gly Ser
65                  70                  75                  80

Gly Asn Trp Gly Thr Thr Ile Ala Lys Val Val Ala Glu Asn Cys Ala
                85                  90                  95

Leu Arg Pro Asn Leu Phe Val Lys Arg Val Asp Met Trp Val Phe Glu
            100                 105                 110

Glu Gln Ile Asp Gly Glu Lys Leu Thr Glu Ile Ile Asn Thr Arg His
        115                 120                 125

Glu Asn Val Lys Tyr Leu Pro Gly Ile Lys Leu Pro Asn Asn Leu Val
130                 135                 140

Ala Asn Pro Asp Ile Val Asp Ala Ala Lys Ala Asp Ile Leu Val
145                 150                 155                 160

Phe Asn Ile Pro His Gln Phe Leu Pro Lys Val Cys Ser Gln Leu Lys
                165                 170                 175

Gly Lys Ile Lys Pro Gln Ala Arg Ala Ile Ser Cys Leu Lys Gly Phe
            180                 185                 190

Asp Val Gly Lys Asp Gly Val Lys Leu Leu Ser Thr Tyr Ile Lys Asp
        195                 200                 205

Thr Leu Asn Ile Glu Cys Gly Ala Leu Ser Gly Ala Asn Leu Ala Pro
    210                 215                 220

Glu Val Ala Lys Glu Asn Trp Ser Glu Thr Thr Val Ala Tyr Gln Ile
225                 230                 235                 240

Pro Glu Asp Tyr Lys Gly Ala Gly Lys Asp Val Asp His Ser Leu Leu
                245                 250                 255

Lys Ala Leu Phe His Arg Pro Tyr Phe His Val Asn Val Ile His Asp
            260                 265                 270

Val Ala Gly Ile Ser Val Ala Gly Ala Leu Lys Asn Val Ile Ala Leu
        275                 280                 285

Gly Cys Gly Tyr Val Glu Gly Leu Gly Trp Gly Asn Asn Ala Ser Ala
    290                 295                 300

Ala Ile Gln Arg Val Gly Leu Ser Glu Met Ile Thr Phe Gly Arg Met
305                 310                 315                 320

Phe Phe Pro Glu Cys Arg Val Glu Thr Phe Tyr Lys Glu Ser Ala Gly
                325                 330                 335

Val Ala Asp Leu Ile Thr Thr Cys Ala Gly Gly Arg Asn Val Arg Val
            340                 345                 350

Ala Lys His Met Ala Ile Thr Gly Lys Ser Ala Leu Glu Ala Glu Lys
        355                 360                 365
```

-continued

Glu Leu Leu Asn Gly Gln Ser Ala Gln Gly Ile Ile Thr Thr Lys Glu
370                 375                 380

Val His Glu Trp Leu Glu Thr Cys Gly Lys Ile Asn Glu Phe Pro Leu
385                 390                 395                 400

Phe Glu Ala Ile Tyr Gln Ile Thr Tyr Gly Asn Ala Ser Met Glu Gln
            405                 410                 415

Ile Pro Glu Met Ile Glu Glu Leu Glu Cys Ile Asp Tyr Asn Val Lys
                420                 425                 430

Lys His

<210> SEQ ID NO 3
<211> LENGTH: 391
<212> TYPE: PRT
<213> ORGANISM: Saccharomyces cerevisiae

<400> SEQUENCE: 3

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
290                 295                 300

```
Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
370                 375                 380

Glu Leu Asp Leu His Glu Asp
385                 390

<210> SEQ ID NO 4
<211> LENGTH: 440
<212> TYPE: PRT
<213> ORGANISM: Saccharomyces cerevisiae

<400> SEQUENCE: 4

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285
```

```
Ile Ala Gly Ala Leu Lys Asn Val Ala Leu Ala Cys Gly Phe Val
    290                 295                 300

Glu Gly Met Gly Trp Gly Asn Asn Ala Ser Ala Ile Gln Arg Leu
305                 310                 315                 320

Gly Leu Gly Glu Ile Ile Lys Phe Gly Arg Met Phe Pro Glu Ser
                325                 330                 335

Lys Val Glu Thr Tyr Tyr Gln Glu Ser Ala Gly Val Ala Asp Leu Ile
                340                 345                 350

Thr Thr Cys Ser Gly Gly Arg Asn Val Lys Val Ala Thr Tyr Met Ala
                355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
                420                 425                 430

Glu Glu Leu Asp Ile Asp Asp Glu
    435                 440

<210> SEQ ID NO 5
<211> LENGTH: 400
<212> TYPE: PRT
<213> ORGANISM: Candida glabrata

<400> SEQUENCE: 5

Met Ser Asn Ser Ala Ala Gly Arg Leu Asn Gln Thr Ser His Ile Leu
1               5                   10                  15

Asn Glu Ser Ile Lys Asn Asp Asp Ile Ser Leu Arg Arg Ser Gln Pro
                20                  25                  30

Ser Thr Thr Ser Leu Gln Ala Leu Glu His Pro Phe Lys Val Thr Val
            35                  40                  45

Ile Gly Ser Gly Asn Trp Gly Thr Thr Ile Ala Lys Val Val Ala Glu
    50                  55                  60

Asn Thr Ala Leu Asn Pro His Leu Phe Val Ser Arg Val Asp Met Trp
65                  70                  75                  80

Val Phe Glu Glu Lys Ile Asp Gly Lys Asn Leu Thr Glu Ile Ile Asn
                85                  90                  95

Glu Gln His Glu Asn Val Lys Tyr Leu Pro Asp Ile Lys Leu Pro Glu
                100                 105                 110

Asn Leu Val Ala Asn Pro Asn Leu Ile Asp Ser Val Lys Gly Ala Asp
            115                 120                 125

Ile Leu Ile Phe Asn Ile Pro His Gln Phe Leu Pro Arg Ile Val Ser
    130                 135                 140

Asn Leu Lys Asn His Val Gly Pro His Val Arg Ala Ile Ser Cys Leu
145                 150                 155                 160

Lys Gly Phe Glu Val Gly Lys Lys Gly Val Gln Leu Leu Ser Ser Tyr
                165                 170                 175

Val Thr Asp Glu Leu Gly Ile Gln Cys Gly Ala Leu Ser Gly Ala Asn
            180                 185                 190

Leu Ala Pro Glu Val Ala Lys Glu His Trp Ser Glu Thr Thr Val Ala
    195                 200                 205

Tyr His Ile Pro Lys Asp Phe Arg Gly Glu Gly Lys Asp Val Asp His
```

```
            210                 215                 220
Lys Leu Leu Lys Ala Leu Phe His Arg Pro Tyr Phe His Val Asn Val
225                 230                 235                 240

Ile Glu Asp Val Ala Gly Ile Ser Ile Ala Gly Ala Leu Lys Asn Val
                    245                 250                 255

Val Ala Leu Gly Cys Gly Phe Val Glu Gly Leu Gly Trp Gly Asn Asn
                260                 265                 270

Ala Ala Ala Ala Ile Gln Arg Val Gly Leu Gly Glu Ile Ile Lys Phe
                275                 280                 285

Gly Gln Met Phe Phe Pro Glu Ser Arg Val Gln Thr Tyr Tyr Gln Glu
            290                 295                 300

Ser Ala Gly Val Ala Asp Leu Ile Thr Thr Cys Ser Gly Gly Arg Asn
305                 310                 315                 320

Val Arg Val Ala Lys His Met Ala Lys Thr Gly Lys Ser Ala Leu Asp
                    325                 330                 335

Ala Glu Lys Glu Leu Leu Asn Gly Gln Ser Ala Gln Gly Ile Ile Thr
                340                 345                 350

Cys Lys Glu Val His Glu Trp Leu Glu Thr Cys Glu Met Thr His Glu
            355                 360                 365

Phe Pro Leu Phe Glu Ala Val Tyr Gln Ile Val Tyr Asn Asn Val Pro
370                 375                 380

Met Lys Asn Leu Pro Asp Met Ile Glu Glu Leu Glu Cys Ile Ala Asp
385                 390                 395                 400

<210> SEQ ID NO 6
<211> LENGTH: 389
<212> TYPE: PRT
<213> ORGANISM: Debaryomyces hansenii

<400> SEQUENCE: 6

Met Ser Gln Tyr Arg Ala Asn Gln Arg Leu Gln Gln Leu Ser Asn Ile
1               5                   10                  15

Leu Arg Pro Asn Gln Leu Ser Ala Glu Lys Ser Leu Lys Pro Glu Thr
            20                  25                  30

Pro Phe Lys Val Ala Val Ile Gly Ser Gly Asn Trp Gly Thr Thr Ile
        35                  40                  45

Ala Lys Val Leu Ala Glu Asn Thr Ala Glu Lys Pro Asp Thr Phe Ala
50                  55                  60

Lys Gln Val Asp Met Trp Val Phe Gln Glu Lys Ile Asp Gly Thr Asn
65                  70                  75                  80

Leu Thr Glu Ile Ile Asn Asn Lys His Glu Asn Val Lys Tyr Leu Pro
                85                  90                  95

Gly Val Lys Leu Pro Glu Asn Leu His Ala Glu Pro Asp Ile Val Lys
            100                 105                 110

Ala Ala Gln Gly Ala Asp Leu Leu Val Phe Asn Leu Pro His Gln Phe
        115                 120                 125

Leu Pro Lys Ile Cys Lys Gln Leu Lys Gly Thr Leu Lys Pro Thr Thr
    130                 135                 140

Arg Ala Ile Ser Cys Leu Lys Gly Leu Glu Val Thr Pro Asp Gly Cys
145                 150                 155                 160

Lys Leu Leu Ser Thr Tyr Ile Thr Glu Asn Leu Gly Ile Glu Cys Gly
                165                 170                 175

Ala Leu Ser Gly Ala Asn Leu Ala Pro Glu Val Ala Arg Cys Lys Trp
            180                 185                 190
```

```
Ser Glu Thr Thr Val Ala Tyr Asn Ile Pro Ala Asp Phe Lys Gly Pro
        195                 200                 205

Gly Lys Asp Ile Asp Ser Ala Val Leu Lys Glu Ala Phe His Arg Pro
    210                 215                 220

Tyr Phe His Val Asn Val Ile Glu Asp Val Ala Gly Val Ser Val Ala
225                 230                 235                 240

Gly Ala Leu Lys Asn Ile Val Ala Ile Ala Val Gly Phe Val Glu Gly
            245                 250                 255

Leu Gly Trp Gly Asp Asn Ala Lys Ser Ala Ile Met Arg Val Gly Leu
        260                 265                 270

Ile Glu Thr Ile Asn Phe Ser Asn Met Phe Pro Asn Ser Lys Pro
        275                 280                 285

Thr Thr Phe Thr His Glu Ser Ala Gly Val Ala Asp Leu Ile Thr Thr
    290                 295                 300

Cys Ser Gly Gly Arg Asn Val Lys Val Gly Arg His Met Ser Lys Thr
305                 310                 315                 320

Gly Glu Ser Ala Glu Glu Ala Glu Lys Lys Leu Leu Asn Gly Gln Ser
            325                 330                 335

Ser Gln Gly Ile Ile Thr Ala Lys Glu Val His Glu Leu Leu Ser Asn
        340                 345                 350

Val Gly Lys Thr Asp Gln Phe Pro Leu Phe Glu Ala Thr Tyr Gln Ile
        355                 360                 365

Ile Tyr Gly Asp Glu Ser Ile Gln Asn Leu Pro Asn Leu Leu Glu Asp
        370                 375                 380

His Ser Leu Phe Lys
385

<210> SEQ ID NO 7
<211> LENGTH: 393
<212> TYPE: PRT
<213> ORGANISM: Pichia jadinii

<400> SEQUENCE: 7

Met Leu Arg Ile Gly Lys Leu Asn Leu Ser Thr Met Ser Ser Ala Gln
1               5                   10                  15

Gln Arg Leu Ala Gln Val Gly Ser His Leu Thr Ala Gln Lys Gln Ser
            20                  25                  30

Leu Ala Pro Gln Arg Pro Tyr Lys Ile Thr Val Ile Gly Ser Gly Asn
        35                  40                  45

Trp Gly Thr Thr Ile Ala Lys Val Leu Ala Glu Asn Ala Gly Leu Arg
    50                  55                  60

Pro His Leu Phe Gln His Gln Val Asp Met Trp Val Phe Glu Glu Lys
65                  70                  75                  80

Ile Asn Gly Val Asn Leu Thr Glu Ile Ile Asn Thr Gln His Glu Asn
            85                  90                  95

Val Lys Tyr Leu Pro Gly Ile Lys Leu Pro Lys Asn Leu His Ala Glu
            100                 105                 110

Pro Ser Ile Val Lys Ala Ala Glu Gly Ala Asp Leu Leu Val Phe Asn
        115                 120                 125

Ile Pro His Gln Phe Leu Pro Gly Ile Cys Lys Gln Leu Ser Lys Ala
    130                 135                 140

Thr Leu Lys Pro His Val Arg Ala Ile Ser Cys Leu Lys Gly Leu Glu
145                 150                 155                 160

Val Thr Pro Asn Gly Cys Lys Leu Leu Ser Thr Tyr Ile Thr Glu His
            165                 170                 175
```

```
Leu Gly Val His Cys Gly Ala Leu Ser Gly Ala Asn Leu Ala Pro Glu
            180                 185                 190

Val Ala Lys Glu Lys Trp Ser Glu Thr Thr Val Ala Tyr Arg Leu Pro
        195                 200                 205

Asn Asp Phe Gln Gly His Gly Lys Asp Ile Asp Arg Tyr Val Leu Arg
210                 215                 220

Ala Ala Phe His Arg Pro Tyr Phe His Val Arg Val Ile Glu Asp Val
225                 230                 235                 240

Ala Gly Val Ser Leu Ala Gly Ala Leu Lys Asn Val Val Ala Leu Gly
                245                 250                 255

Val Gly Phe Val His Gly Leu Asn Trp Gly Asp Asn Ala Ala Ser Ala
            260                 265                 270

Ile Gln Arg Phe Gly Leu Asn Glu Thr Ile Lys Phe Ala Glu Val Phe
        275                 280                 285

Phe Pro Gly Glu Thr Asn Gln Asp Thr Phe Thr Lys Glu Ser Ala Gly
    290                 295                 300

Val Ala Asp Leu Ile Thr Thr Cys Ser Gly Gly Arg Asn Val Arg Val
305                 310                 315                 320

Ala Lys Ala Met Ala Ile Thr Gly Lys Ser Ala Val Glu Val Glu Arg
                325                 330                 335

Glu Leu Leu Asn Gly Gln Ser Ala Gln Gly Ile Ile Thr Ser Lys Glu
            340                 345                 350

Val His Glu Leu Leu Ala Ala Lys Asn Leu Thr Lys Glu Phe Pro Leu
        355                 360                 365

Phe Glu Ala Ile Tyr Gln Ile Val Tyr Gly Thr Glu Ser Ile Glu Arg
    370                 375                 380

Leu Pro Glu Leu Ile Glu Glu Asp Glu
385                 390

<210> SEQ ID NO 8
<211> LENGTH: 248
<212> TYPE: PRT
<213> ORGANISM: Kluyveromyces marxianus

<400> SEQUENCE: 8

Met Ser Ala Ala Pro Ile Ser Leu Arg Val Asn Ala Ala Leu Phe Asp
1               5                   10                  15

Val Asp Gly Thr Leu Ile Ile Ser Gln Gly Ala Ile Ala Glu Phe Trp
            20                  25                  30

Arg Asp Phe Gly Lys Asp Lys Pro Tyr Phe Asp Ser Gln His Val Ile
        35                  40                  45

Asp Ile Ser His Gly Trp Arg Thr Tyr Asp Val Ile Lys Lys Phe Ala
    50                  55                  60

Pro Asp Tyr Ala Asn Glu Glu Tyr Val Thr Lys Leu Glu Gly Glu Ile
65                  70                  75                  80

Pro Asp Lys Phe Gly Lys His Ala Ile Glu Val Pro Gly Ala Ile Lys
                85                  90                  95

Leu Cys Ala Ala Leu Asn Ala Leu Pro Lys Glu Lys Trp Ala Val Ala
            100                 105                 110

Thr Ser Gly Thr Phe Glu Met Ala His Lys Trp Phe Asp Ile Leu Gly
        115                 120                 125

Ile Lys Arg Pro Ser Asn Phe Ile Thr Ala Asn Asp Val Lys Asn Gly
    130                 135                 140

Lys Pro His Pro Glu Pro Tyr Leu Lys Gly Arg Asn Gly Leu Gly Tyr
```

-continued

```
              145                 150                 155                 160
        Pro Ile Asn Glu Ala Asn Pro Ala Ala Ser Lys Val Ile Val Phe Glu
                        165                 170                 175

Asp Ala Pro Ala Gly Ile Leu Ala Gly Lys Ala Ala Gly Cys Lys Ile
                        180                 185                 190

Val Gly Ile Ala Thr Thr Phe Asp Lys Glu Phe Leu Ile Glu Lys Gly
                        195                 200                 205

Cys Asp Ile Val Ile Lys Asp His Thr Lys Leu Arg Val Ala Ala Tyr
        210                 215                 220

His Pro Glu Thr Asp Glu Val Glu Phe Val Phe Asp Glu Tyr Leu Tyr
        225                 230                 235                 240

Ala Lys Asp Asp Leu Leu Glu Trp
                        245

<210> SEQ ID NO 9
<211> LENGTH: 250
<212> TYPE: PRT
<213> ORGANISM: Saccharomyces cerevisiae

<400> SEQUENCE: 9

Met Gly Leu Thr Thr Lys Pro Leu Ser Leu Lys Val Asn Ala Ala Leu
        1               5                   10                  15

Phe Asp Val Asp Gly Thr Ile Ile Ser Gln Pro Ala Ile Ala Ala
                        20                  25                  30

Phe Trp Arg Asp Phe Gly Lys Asp Lys Pro Tyr Phe Asp Ala Glu His
                        35                  40                  45

Val Ile Gln Val Ser His Gly Trp Arg Thr Phe Asp Ala Ile Ala Lys
        50                  55                  60

Phe Ala Pro Asp Phe Ala Asn Glu Glu Tyr Val Asn Lys Leu Glu Ala
        65                  70                  75                  80

Glu Ile Pro Val Lys Tyr Gly Glu Lys Ser Ile Glu Val Pro Gly Ala
                        85                  90                  95

Val Lys Leu Cys Asn Ala Leu Asn Ala Leu Pro Lys Glu Lys Trp Ala
                        100                 105                 110

Val Ala Thr Ser Gly Thr Arg Asp Met Ala Gln Lys Trp Phe Glu His
                        115                 120                 125

Leu Gly Ile Arg Arg Pro Lys Tyr Phe Ile Thr Ala Asn Asp Val Lys
        130                 135                 140

Gln Gly Lys Pro His Pro Glu Pro Tyr Leu Lys Gly Arg Asn Gly Leu
        145                 150                 155                 160

Gly Tyr Pro Ile Asn Glu Gln Asp Pro Ser Lys Ser Lys Val Val Val
                        165                 170                 175

Phe Glu Asp Ala Pro Ala Gly Ile Ala Ala Gly Lys Ala Ala Gly Cys
                        180                 185                 190

Lys Ile Ile Gly Ile Ala Thr Thr Phe Asp Leu Asp Phe Leu Lys Glu
                        195                 200                 205

Lys Gly Cys Asp Ile Ile Val Lys Asn His Glu Ser Ile Arg Val Gly
        210                 215                 220

Gly Tyr Asn Ala Glu Thr Asp Glu Val Glu Phe Ile Phe Asp Asp Tyr
        225                 230                 235                 240

Leu Tyr Ala Lys Asp Asp Leu Leu Lys Trp
                        245                 250

<210> SEQ ID NO 10
<211> LENGTH: 271
```

<212> TYPE: PRT
<213> ORGANISM: Saccharomyces cerevisiae

<400> SEQUENCE: 10

```
Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
        35                  40                  45

Pro Ala Ile Ala Ala Phe Trp Arg Asp Phe Gly Lys Asp Lys Pro Tyr
50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
        195                 200                 205

Lys Ala Ala Gly Cys Lys Ile Val Gly Ile Ala Thr Thr Phe Asp Leu
210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Asp Leu Leu Lys Trp
            260                 265                 270
```

<210> SEQ ID NO 11
<211> LENGTH: 236
<212> TYPE: PRT
<213> ORGANISM: Schizosaccharomyces pombe

<400> SEQUENCE: 11

```
Met Ile Pro Glu Ala Cys Leu Phe Asp Met Asp Gly Leu Leu Val Asp
1               5                   10                  15

Thr Glu Ser Ile Tyr Thr Lys Ser Thr Asn Ile Ile Leu Lys Arg Tyr
            20                  25                  30

Asn Lys Gly Pro Phe Ser Met Glu Val Lys Ala Lys Met Met Gly Arg
        35                  40                  45

Thr Ser Lys Glu Ala Ser Arg Ile Phe Leu Asp Trp Ser Gly Ile Asp
50                  55                  60

Leu Thr Cys Glu Glu Tyr Ile Ala Leu Gln Arg Glu Thr Gln Ala Glu
65                  70                  75                  80
```

-continued

```
Leu Trp Arg His Thr Lys Pro Leu Pro Gly Val Met Asn Leu Leu Ser
                85                  90                  95

Lys Leu Lys Ser Leu Asn Ile Pro Ile Ala Leu Ala Thr Ser Ser Asp
            100                 105                 110

Thr His Asn Phe Glu Lys Lys Ser Ala His Leu Ser His Leu Phe Asp
        115                 120                 125

His Phe Asp Gly Asn Ile Ile Thr Gly Asp Pro Arg Leu Pro Val
    130                 135                 140

Gly Arg Gly Lys Pro His Pro Asp Ile Trp Phe Ile Ala Leu Lys Met
145                 150                 155                 160

Ile Asn Asp Lys Arg Lys Ala Gln Gly Gln Ala Glu Ile Leu Pro Glu
                165                 170                 175

Asn Cys Leu Val Phe Glu Asp Ser Ile Thr Gly Val Gln Ser Gly Arg
            180                 185                 190

Ala Ala Gly Met Lys Val Val Trp Val Pro Asp Val Asn Ile Leu Pro
        195                 200                 205

Phe Phe Ser Leu Ser Pro Glu Gln Ala Ala Asp Lys His Ile Thr Lys
    210                 215                 220

Val Leu Ser Leu Glu Asn Phe Asp Val Thr Lys Val
225                 230                 235

<210> SEQ ID NO 12
<211> LENGTH: 246
<212> TYPE: PRT
<213> ORGANISM: Schizosaccharomyces pombe

<400> SEQUENCE: 12

Met Ala Ala Lys His Val Lys Tyr Met Ala Cys Leu Phe Asp Met Asp
1               5                   10                  15

Gly Leu Leu Val Asp Ser Glu Thr Ile Tyr Thr Lys Thr Thr Asn Leu
            20                  25                  30

Ile Leu Asp Arg Tyr Gly Lys Asp Pro Leu Pro Ile Ser Val Lys Ala
        35                  40                  45

Gln Met Met Gly Arg Pro Gly Ser Ala Ala Lys Val Val Ile Asp
    50                  55                  60

Trp Ser Asn Ile Pro Met Thr Pro Gln Gln Phe Val Asp Glu Gln Gln
65                  70                  75                  80

Val Ile Arg Ala Lys Phe Trp Ser Ser Leu Lys Pro Met Pro Gly Ala
                85                  90                  95

Glu Ser Leu Ile Asn Asn Leu Ser Asn His Gly Ile Asp Ile Gly Val
            100                 105                 110

Cys Thr His Pro Tyr Ala Ile Ile Lys Thr Ala His Leu Lys His Ile
        115                 120                 125

Phe Glu Lys Phe Gly Lys Asn Val Ile Thr Gly Asp Asn Pro Ser Ile
    130                 135                 140

Ala Pro Gly Arg Gly Lys Pro Phe Pro Asp Ile Trp Leu Lys Val Leu
145                 150                 155                 160

Asn Leu Ile Asn Glu Ser Arg Lys Gln Arg Gly Leu Lys Ala Leu Thr
                165                 170                 175

Pro Ser Gln Cys Ile Ala Phe Glu Asp Ser Ile Pro Gly Val Lys Ser
            180                 185                 190

Ala Lys Ala Ala Gly Met His Val Ile Trp Val Pro Asp Ala Ala Ile
        195                 200                 205

Lys Asn Leu Val Gly Asp Gln Leu Asn Glu Ile Val Asp Ser Gln Cys
    210                 215                 220
```

Glu Thr Leu Pro Ser Leu Ser Glu Phe Asp Ile Asn Lys Tyr Leu Asn
225                 230                 235                 240

Ile Asn Ser Lys Gln Ala
                245

<210> SEQ ID NO 13
<211> LENGTH: 450
<212> TYPE: PRT
<213> ORGANISM: Schizosaccharomyces pombe

<400> SEQUENCE: 13

Met Ile Gly Pro Arg Leu Cys Ala Ala Thr Pro Arg Phe Pro Leu Val
1               5                   10                  15

Ser Leu Ala His Arg Asn Ser Lys Val Phe Ala Leu Ala Ser Ser Asn
                20                  25                  30

Ala Val Ala Gln Arg Trp Gly Lys Arg Phe Tyr Ala Pro Ile Glu Thr
            35                  40                  45

Glu Thr Pro His Lys Val Gly Val Glu Phe Glu Ser Lys Asp Arg
    50                  55                  60

Ile Phe Thr Ser Pro Gln Lys Tyr Val Gln Gly Arg His Ala Phe Thr
65                  70                  75                  80

Arg Ser Tyr Met Tyr Val Lys Lys Trp Ala Thr Lys Ser Ala Val Val
                85                  90                  95

Leu Ala Asp Gln Asn Val Trp Asn Ile Cys Ala Asn Lys Ile Val Asp
            100                 105                 110

Ser Leu Ser Gln Asn Gly Met Thr Val Thr Lys Leu Val Phe Gly Gly
        115                 120                 125

Glu Ala Ser Leu Val Glu Leu Asp Lys Leu Arg Lys Gln Cys Pro Asp
130                 135                 140

Asp Thr Gln Val Ile Ile Gly Val Gly Gly Lys Thr Met Asp Ser
145                 150                 155                 160

Ala Lys Tyr Ile Ala His Ser Met Asn Leu Pro Ser Ile Ile Cys Pro
                165                 170                 175

Thr Thr Ala Ser Ser Asp Ala Ala Thr Ser Ser Leu Ser Val Ile Tyr
            180                 185                 190

Thr Pro Asp Gly Gln Phe Gln Lys Tyr Ser Phe Tyr Pro Leu Asn Pro
        195                 200                 205

Asn Leu Ile Phe Ile Asp Thr Asp Val Ile Val Arg Ala Pro Val Arg
210                 215                 220

Phe Leu Ile Ser Gly Ile Gly Asp Ala Leu Ser Thr Trp Val Glu Thr
225                 230                 235                 240

Glu Ser Val Ile Arg Ser Asn Ser Thr Ser Phe Ala Gly Gly Val Ala
                245                 250                 255

Ser Ile Ala Gly Arg Tyr Ile Ala Arg Ala Cys Lys Asp Thr Leu Glu
            260                 265                 270

Lys Tyr Ala Leu Ser Ala Ile Leu Ser Asn Thr Arg Gly Val Cys Thr
        275                 280                 285

Glu Ala Phe Glu Asn Val Val Glu Ala Asn Thr Leu Met Ser Gly Leu
290                 295                 300

Gly Phe Glu Asn Gly Gly Leu Ala Ala Ala His Ala Ile His Asn Gly
305                 310                 315                 320

Met Thr Ala Ile His Gly Pro Val His Arg Leu Met His Gly Glu Lys
                325                 330                 335

Val Ala Tyr Gly Thr Leu Val Gln Val Val Leu Glu Asp Trp Pro Leu

```
                340             345             350
Glu Asp Phe Asn Asn Leu Ala Ser Phe Met Ala Lys Cys His Leu Pro
            355                 360                 365

Ile Thr Leu Glu Glu Leu Gly Ile Pro Asn Val Thr Asp Glu Glu Leu
    370                 375                 380

Leu Met Val Gly Arg Ala Thr Leu Arg Pro Asp Glu Ser Ile His Asn
385                 390                 395                 400

Met Ser Lys Lys Phe Asn Pro Ser Gln Ile Ala Asp Ala Ile Lys Ala
                405                 410                 415

Val Asp Ser Tyr Ser Gln Lys Trp Gln Glu Gln Thr Gly Trp Thr Glu
            420                 425                 430

Arg Phe Arg Leu Pro Pro Ser Arg His Ser Pro His Leu Thr Asp Ile
                435                 440                 445

His Pro
    450

<210> SEQ ID NO 14
<211> LENGTH: 32
<212> TYPE: DNA
<213> ORGANISM: Artificial
<220> FEATURE:
<223> OTHER INFORMATION: Primer

<400> SEQUENCE: 14
aaaaaaacgc gtggtggtga cccatccata ac                                     32

<210> SEQ ID NO 15
<211> LENGTH: 30
<212> TYPE: DNA
<213> ORGANISM: Artificial
<220> FEATURE:
<223> OTHER INFORMATION: Primer

<400> SEQUENCE: 15 tttttctgc agatcgatgg cgcgaacaag                                         30

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
aaaaaagacg tcgaagagaa tcggactagg                                        30

<210> SEQ ID NO 17
<211> LENGTH: 30
<212> TYPE: DNA
<213> ORGANISM: Artificial
<220> FEATURE:
<223> OTHER INFORMATION: Primer

<400> SEQUENCE: 17 tttttgccg gcggatggag ggacaaatac                                         30

<210> SEQ ID NO 18
<211> LENGTH: 20
<212> TYPE: DNA
<213> ORGANISM: Artificial
<220> FEATURE:
<223> OTHER INFORMATION: Primer
```

<400> SEQUENCE: 18
tggcggtagt cacaaggacg                                           20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
agtgccgagg accgagaatc                                           20

<210> SEQ ID NO 20
<211> LENGTH: 32
<212> TYPE: DNA
<213> ORGANISM: Artificial
<220> FEATURE:
<223> OTHER INFORMATION: Primer

<400> SEQUENCE: 20
aaaaaaacgc gtgtccctcc cacttacaac tc                             32

<210> SEQ ID NO 21
<211> LENGTH: 32
<212> TYPE: DNA
<213> ORGANISM: Artificial
<220> FEATURE:
<223> OTHER INFORMATION: Primer

<400> SEQUENCE: 21 tttttggta ccccggaacc catctggaaa tc                              32

<210> SEQ ID NO 22
<211> LENGTH: 32
<212> TYPE: DNA
<213> ORGANISM: Artificial
<220> FEATURE:
<223> OTHER INFORMATION: Primer

<400> SEQUENCE: 22
aaaaaaacta gttaggtcgc tggatgtcct ac                             32

<210> SEQ ID NO 23
<211> LENGTH: 30
<212> TYPE: DNA
<213> ORGANISM: Artificial
<220> FEATURE:
<223> OTHER INFORMATION: Primer

<400> SEQUENCE: 23 tttttgccg gcaagtcggg catagaaggc                                 30

<210> SEQ ID NO 24
<211> LENGTH: 21
<212> TYPE: DNA
<213> ORGANISM: Artificial
<220> FEATURE:
<223> OTHER INFORMATION: Primer

<400> SEQUENCE: 24
ggkgctaach tbgcymcmga r                                         21

<210> SEQ ID NO 25
<211> LENGTH: 21

```
<212> TYPE: DNA
<213> ORGANISM: Artificial
<220> FEATURE:
<223> OTHER INFORMATION: Primer

<400> SEQUENCE: 25
dgtratbara tcrgcvacac c                                              21

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
krtygghycy ggtaactggg g                                              21

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
rtgraagtad ggtckgtgga a                                              21

<210> SEQ ID NO 28
<211> LENGTH: 27
<212> TYPE: DNA
<213> ORGANISM: Artificial
<220> FEATURE:
<223> OTHER INFORMATION: Primer

<400> SEQUENCE: 28
ccattgccgg tgcactcaag aatgtcg                                        27

<210> SEQ ID NO 29
<211> LENGTH: 27
<212> TYPE: DNA
<213> ORGANISM: Artificial
<220> FEATURE:
<223> OTHER INFORMATION: Primer

<400> SEQUENCE: 29
cgacattctt gagtgcaccg gcaatgg                                        27

<210> SEQ ID NO 30
<211> LENGTH: 27
<212> TYPE: DNA
<213> ORGANISM: Artificial
<220> FEATURE:
<223> OTHER INFORMATION: Primer

<400> SEQUENCE: 30
ggctgctgga tttgtcgaag gtttagg                                        27

<210> SEQ ID NO 31
<211> LENGTH: 27
<212> TYPE: DNA
<213> ORGANISM: Artificial
<220> FEATURE:
<223> OTHER INFORMATION: Primer

<400> SEQUENCE: 31
```

```
ccttgccttt acctctgaaa tcgtccg                                          27
```

<210> SEQ ID NO 32
<211> LENGTH: 32
<212> TYPE: DNA
<213> ORGANISM: Artificial
<220> FEATURE:
<223> OTHER INFORMATION: Primer

<400> SEQUENCE: 32

```
tccccggtcg accggaactt agcttactcg tc                                    32
```

<210> SEQ ID NO 33
<211> LENGTH: 32
<212> TYPE: DNA
<213> ORGANISM: Artificial
<220> FEATURE:
<223> OTHER INFORMATION: Primer

<400> SEQUENCE: 33

```
ttgcgaggat cctgagtgca gtagctgtac ac                                    32
```

<210> SEQ ID NO 34
<211> LENGTH: 706
<212> TYPE: DNA
<213> ORGANISM: Kluyveromyces thermotolerans

<400> SEQUENCE: 34

```
cactcgcaag ctgtgccatc gcccaacggt taattataag aaatcaacat cagccaacaa      60
ctattttcgt ccccctcttt tcagtggtaa cgagcaatta cattagtaag agactatttt     120
cttcagtgat ttgtaatttt ttttcagtga tttgtaattc tttctcgaaa tatgcgggct     180
waamtaatcc ggacattcac tacatgcaag gaaaaacgag aaccgcggag atttcctcag     240
taagtaacaa tgatgatctt tttacgcttc atcatcactt tccaaagttc taagctataa     300
gttcaagcct agatacgctg aaaaactcct gaccaacaat gtaaagaaaa caattacaat     360
tgtaaggttg aaaacatcta aaaatgaaat attttattgt acatgcacac cctgatagtc     420
attctcttac ttcatccctg aaagacgtgg ctgtacaaga gttggaatcg caaggtcatg     480
aggttaaagt tagtgatctt tatgctcaaa agtggaaggc ctcaatagac cgtgacgacw     540
wmaaaaaama aamrmaagaa gagaggttaa aaatacccca agcttcttat gaagcgtatg     600
ccagaggagc attaacaaaa gacgtaaatc aggaacagga aaaacttatt tgggcggact     660
ttgtcatttt gtcgtttcct atatggtggt cttctatgcc ggctag                    706
```

<210> SEQ ID NO 35
<211> LENGTH: 30
<212> TYPE: DNA
<213> ORGANISM: Artificial
<220> FEATURE:
<223> OTHER INFORMATION: Primer

<400> SEQUENCE: 35

```
tgtcagcatg cactcgcaag ctgtgccatc                                       30
```

<210> SEQ ID NO 36
<211> LENGTH: 33
<212> TYPE: DNA
<213> ORGANISM: Artificial
<220> FEATURE:
<223> OTHER INFORMATION: Primer

<400> SEQUENCE: 36

```
aaccttgtcg actagccggc atagaagacc acc                                    33

<210> SEQ ID NO 37
<211> LENGTH: 30
<212> TYPE: DNA
<213> ORGANISM: Artificial
<220> FEATURE:
<223> OTHER INFORMATION: Primer

<400> SEQUENCE: 37
tgtcaggatc cactcgcaag ctgtgccatc                                        30

<210> SEQ ID NO 38
<211> LENGTH: 33
<212> TYPE: DNA
<213> ORGANISM: Artificial
<220> FEATURE:
<223> OTHER INFORMATION: Primer

<400> SEQUENCE: 38
aaccttcccg ggtagccggc atagaagacc acc                                    33

<210> SEQ ID NO 39
<211> LENGTH: 23
<212> TYPE: DNA
<213> ORGANISM: Artificial
<220> FEATURE:
<223> OTHER INFORMATION: Primer

<400> SEQUENCE: 39
aaccaaagaa ttgttgctgc ttt                                               23

<210> SEQ ID NO 40
<211> LENGTH: 25
<212> TYPE: DNA
<213> ORGANISM: Artificial
<220> FEATURE:
<223> OTHER INFORMATION: Primer

<400> SEQUENCE: 40
ttcgaaaaca cctggtggac cgttc                                             25

<210> SEQ ID NO 41
<211> LENGTH: 25
<212> TYPE: DNA
<213> ORGANISM: Artificial
<220> FEATURE:
<223> OTHER INFORMATION: Primer

<400> SEQUENCE: 41
gcggtgaccc gggagatctg aattc                                             25

<210> SEQ ID NO 42
<211> LENGTH: 12
<212> TYPE: DNA
<213> ORGANISM: Artificial
<220> FEATURE:
<223> OTHER INFORMATION: Primer

<400> SEQUENCE: 42
gaattcagat ct                                                           12

<210> SEQ ID NO 43
<211> LENGTH: 25
<212> TYPE: DNA
```

```
<213> ORGANISM: Artificial
<220> FEATURE:
<223> OTHER INFORMATION: Primer

<400> SEQUENCE: 43
gcggtgaccc gggagatctg aattc                                         25

<210> SEQ ID NO 44
<211> LENGTH: 27
<212> TYPE: DNA
<213> ORGANISM: Artificial
<220> FEATURE:
<223> OTHER INFORMATION: Primer

<400> SEQUENCE: 44
ccaattctgc agcaactggc tttaacg                                       27

<210> SEQ ID NO 45
<211> LENGTH: 25
<212> TYPE: DNA
<213> ORGANISM: Artificial
<220> FEATURE:
<223> OTHER INFORMATION: Primer

<400> SEQUENCE: 45
gcggtgaccc gggagatctg aattc                                         25

<210> SEQ ID NO 46
<211> LENGTH: 21
<212> TYPE: DNA
<213> ORGANISM: Artificial
<220> FEATURE:
<223> OTHER INFORMATION: Primer

<400> SEQUENCE: 46
gcctcaccat ttggtctgcc c                                             21

<210> SEQ ID NO 47
<211> LENGTH: 25
<212> TYPE: DNA
<213> ORGANISM: Artificial
<220> FEATURE:
<223> OTHER INFORMATION: Primer

<400> SEQUENCE: 47
gactccccgg agtgtcgaaa tatga                                         25

<210> SEQ ID NO 48
<211> LENGTH: 24
<212> TYPE: DNA
<213> ORGANISM: Artificial
<220> FEATURE:
<223> OTHER INFORMATION: Primer

<400> SEQUENCE: 48
gtgatagcgg gtcctttcgc tacc                                          24

<210> SEQ ID NO 49
<211> LENGTH: 25
<212> TYPE: DNA
<213> ORGANISM: Artificial
<220> FEATURE:
<223> OTHER INFORMATION: Primer

<400> SEQUENCE: 49
gcggtgaccc gggagatctg aattc                                         25
```

<210> SEQ ID NO 50
<211> LENGTH: 12
<212> TYPE: DNA
<213> ORGANISM: Artificial
<220> FEATURE:
<223> OTHER INFORMATION: Primer

<400> SEQUENCE: 50
gaattcagat ct                                                          12

<210> SEQ ID NO 51
<211> LENGTH: 36
<212> TYPE: DNA
<213> ORGANISM: Artificial
<220> FEATURE:
<223> OTHER INFORMATION: Primer

<400> SEQUENCE: 51
gcgatctcga gatttgctgc aacggcaaca tcaatg                                36

<210> SEQ ID NO 52
<211> LENGTH: 36
<212> TYPE: DNA
<213> ORGANISM: Artificial
<220> FEATURE:
<223> OTHER INFORMATION: Primer

<400> SEQUENCE: 52
ctagcatctg attgttgttg tcgttgtttt tgtttt                                36

<210> SEQ ID NO 53
<211> LENGTH: 36
<212> TYPE: DNA
<213> ORGANISM: Artificial
<220> FEATURE:
<223> OTHER INFORMATION: Primer

<400> SEQUENCE: 53
gcgatctcga gatttgctgc aacggcaaca tcaatg                                36

<210> SEQ ID NO 54
<211> LENGTH: 36
<212> TYPE: DNA
<213> ORGANISM: Artificial
<220> FEATURE:
<223> OTHER INFORMATION: Primer

<400> SEQUENCE: 54
acttggccat ggttgttgtt gttgtcgttg tttttg                                36

<210> SEQ ID NO 55
<211> LENGTH: 44
<212> TYPE: DNA
<213> ORGANISM: Artificial
<220> FEATURE:
<223> OTHER INFORMATION: Primer

<400> SEQUENCE: 55
ccggaattcg atatctgggc wggkaatgcc aaygarttra atgc                       44

<210> SEQ ID NO 56
<211> LENGTH: 44
<212> TYPE: DNA
<213> ORGANISM: Artificial
<220> FEATURE:

```
<223> OTHER INFORMATION: Primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 56
cgcggattca ggcctcagta ngaraawgaa ccngtrttra artc                44

<210> SEQ ID NO 57
<211> LENGTH: 36
<212> TYPE: DNA
<213> ORGANISM: Artificial
<220> FEATURE:
<223> OTHER INFORMATION: Primer

<400> SEQUENCE: 57
actgtcgagc tcagtatatg gaattgacgg ctcatc                         36

<210> SEQ ID NO 58
<211> LENGTH: 38
<212> TYPE: DNA
<213> ORGANISM: Artificial
<220> FEATURE:
<223> OTHER INFORMATION: Primer

<400> SEQUENCE: 58
actgacgcgt cgacgtatca tttgtagccc acgccacc                       38

<210> SEQ ID NO 59
<211> LENGTH: 35
<212> TYPE: DNA
<213> ORGANISM: Artificial
<220> FEATURE:
<223> OTHER INFORMATION: Primer

<400> SEQUENCE: 59
cctcccccgg gctgatagaa gggtgatatg taatt                          35

<210> SEQ ID NO 60
<211> LENGTH: 24
<212> TYPE: DNA
<213> ORGANISM: Artificial
<220> FEATURE:
<223> OTHER INFORMATION: Primer

<400> SEQUENCE: 60
ccaagagtta tggggcccca gttg                                      24

<210> SEQ ID NO 61
<211> LENGTH: 36
<212> TYPE: DNA
<213> ORGANISM: Artificial
<220> FEATURE:
<223> OTHER INFORMATION: Primer

<400> SEQUENCE: 61
gcgatctcga gatttgctgc aacggcaaca tcaatg                         36

<210> SEQ ID NO 62
<211> LENGTH: 69
<212> TYPE: DNA
<213> ORGANISM: Artificial
```

```
<220> FEATURE:
<223> OTHER INFORMATION: Primer

<400> SEQUENCE: 62
tggactagta catgcatgcg gtgagaaagt agaaagcaaa cattgttgtt gttgttgtcg      60
ttgtttttg                                                             69

<210> SEQ ID NO 63
<211> LENGTH: 42
<212> TYPE: DNA
<213> ORGANISM: Artificial
<220> FEATURE:
<223> OTHER INFORMATION: Primer

<400> SEQUENCE: 63
cctcccccgg ggatatcaaa gttatattat taatgattca ag                        42

<210> SEQ ID NO 64
<211> LENGTH: 43
<212> TYPE: DNA
<213> ORGANISM: Artificial
<220> FEATURE:
<223> OTHER INFORMATION: Primer

<400> SEQUENCE: 64
ggacgagagc tcgggcccat gacttcagag ttgattttga gtc                       43

<210> SEQ ID NO 65
<211> LENGTH: 44
<212> TYPE: DNA
<213> ORGANISM: Artificial
<220> FEATURE:
<223> OTHER INFORMATION: Primer

<400> SEQUENCE: 65
ggacatgcat gcgagctcaa tgcgtgacac cgccatgatg gttg                      44

<210> SEQ ID NO 66
<211> LENGTH: 52
<212> TYPE: DNA
<213> ORGANISM: Artificial
<220> FEATURE:
<223> OTHER INFORMATION: Primer

<400> SEQUENCE: 66
ggacatgcat gctacgtacc ctgcagggca ccaacagcaa cacccacctg aa              52

<210> SEQ ID NO 67
<211> LENGTH: 43
<212> TYPE: DNA
<213> ORGANISM: Artificial
<220> FEATURE:
<223> OTHER INFORMATION: Primer

<400> SEQUENCE: 67
ggacatgcat gcgagctcat agttgaacaa acactggcat ttg                       43

<210> SEQ ID NO 68
<211> LENGTH: 52
<212> TYPE: DNA
<213> ORGANISM: Artificial
<220> FEATURE:
<223> OTHER INFORMATION: Primer

<400> SEQUENCE: 68
```
ggacatgcat gctacgtacc ctgcaggtgt gtgcaactag gtttatgtgg ag            52

<210> SEQ ID NO 69
<211> LENGTH: 53
<212> TYPE: DNA
<213> ORGANISM: Artificial
<220> FEATURE:
<223> OTHER INFORMATION: Primer

<400> SEQUENCE: 69
cctcccccgg ggatatctag ttagatagct cctcctccaa tcgaattatt agc           53

<210> SEQ ID NO 70
<211> LENGTH: 42
<212> TYPE: DNA
<213> ORGANISM: Artificial
<220> FEATURE:
<223> OTHER INFORMATION: Primer

<400> SEQUENCE: 70
ggacgagagc tcgggcccta cgtctatgta tcataaattt gg                       42

<210> SEQ ID NO 71
<211> LENGTH: 33
<212> TYPE: DNA
<213> ORGANISM: Artificial
<220> FEATURE:
<223> OTHER INFORMATION: Primer

<400> SEQUENCE: 71
aaaaaacata tggagatgtt aatatgtggg tct                                 33

<210> SEQ ID NO 72
<211> LENGTH: 33
<212> TYPE: DNA
<213> ORGANISM: Artificial
<220> FEATURE:
<223> OTHER INFORMATION: Primer

<400> SEQUENCE: 72 tttttcctg caggtcagta ataacagtgg aga                                  33

<210> SEQ ID NO 73
<211> LENGTH: 30
<212> TYPE: DNA
<213> ORGANISM: Artificial
<220> FEATURE:
<223> OTHER INFORMATION: Primer

<400> SEQUENCE: 73
aaaaaacccg gggtgcctta tcaggtgcta                                     30

<210> SEQ ID NO 74
<211> LENGTH: 30
<212> TYPE: DNA
<213> ORGANISM: Artificial
<220> FEATURE:
<223> OTHER INFORMATION: Primer

<400> SEQUENCE: 74 tttttgaat tcaaggttgc agcatgacag                                      30

<210> SEQ ID NO 75
<211> LENGTH: 20
<212> TYPE: DNA
<213> ORGANISM: Artificial

<220> FEATURE:
<223> OTHER INFORMATION: Primer

<400> SEQUENCE: 75
gagttcaccc gtccagatag                                                20

<210> SEQ ID NO 76
<211> LENGTH: 22
<212> TYPE: DNA
<213> ORGANISM: Artificial
<220> FEATURE:
<223> OTHER INFORMATION: Primer

<400> SEQUENCE: 76
ggacaacgta catggacgat tc                                             22

<210> SEQ ID NO 77
<211> LENGTH: 20
<212> TYPE: DNA
<213> ORGANISM: Artificial
<220> FEATURE:
<223> OTHER INFORMATION: Primer

<400> SEQUENCE: 77
ctatctggac gggtgaactc                                                20

<210> SEQ ID NO 78
<211> LENGTH: 18
<212> TYPE: DNA
<213> ORGANISM: Artificial
<220> FEATURE:
<223> OTHER INFORMATION: Primer

<400> SEQUENCE: 78
ggactggggg tgtacaat                                                  18

<210> SEQ ID NO 79
<211> LENGTH: 20
<212> TYPE: DNA
<213> ORGANISM: Artificial
<220> FEATURE:
<223> OTHER INFORMATION: Primer

<400> SEQUENCE: 79
cttgtgcagg ctcagacttg                                                20

<210> SEQ ID NO 80
<211> LENGTH: 20
<212> TYPE: DNA
<213> ORGANISM: Artificial
<220> FEATURE:
<223> OTHER INFORMATION: Primer

<400> SEQUENCE: 80
caaggcattc tggcagcttc                                                20

<210> SEQ ID NO 81
<211> LENGTH: 22
<212> TYPE: DNA
<213> ORGANISM: Artificial
<220> FEATURE:
<223> OTHER INFORMATION: Primer

<400> SEQUENCE: 81
cggcttccaa agcggactta cc                                             22

<210> SEQ ID NO 82
<211> LENGTH: 22
<212> TYPE: DNA
<213> ORGANISM: Artificial
<220> FEATURE:
<223> OTHER INFORMATION: Primer

<400> SEQUENCE: 82
aaggccgaca gcccattcaa gg                                             22

<210> SEQ ID NO 83
<211> LENGTH: 25
<212> TYPE: DNA
<213> ORGANISM: Artificial
<220> FEATURE:
<223> OTHER INFORMATION: Primer

<400> SEQUENCE: 83
gatacgtcga ccgcgatctc gagcg                                          25

<210> SEQ ID NO 84
<211> LENGTH: 34
<212> TYPE: DNA
<213> ORGANISM: Artificial
<220> FEATURE:
<223> OTHER INFORMATION: Primer

<400> SEQUENCE: 84
gttactagtg gtacagagaa cttgtaaaca attc                                34

<210> SEQ ID NO 85
<211> LENGTH: 27
<212> TYPE: DNA
<213> ORGANISM: Artificial
<220> FEATURE:
<223> OTHER INFORMATION: Primer

<400> SEQUENCE: 85
ggttatagcg gaaaacaccg ttgagag                                        27

<210> SEQ ID NO 86
<211> LENGTH: 23
<212> TYPE: DNA
<213> ORGANISM: Artificial
<220> FEATURE:
<223> OTHER INFORMATION: Primer

<400> SEQUENCE: 86
ccgctagacc aacagtcatc tag                                            23

<210> SEQ ID NO 87
<211> LENGTH: 23
<212> TYPE: DNA
<213> ORGANISM: Artificial
<220> FEATURE:
<223> OTHER INFORMATION: Primer

<400> SEQUENCE: 87
cttctatagg ttgagaccct cgg                                            23

<210> SEQ ID NO 88
<211> LENGTH: 26
<212> TYPE: DNA
<213> ORGANISM: Artificial
<220> FEATURE:
<223> OTHER INFORMATION: Primer

```
<400> SEQUENCE: 88
gtgccatata tctaccaact ctaacg                                    26

<210> SEQ ID NO 89
<211> LENGTH: 26
<212> TYPE: DNA
<213> ORGANISM: Artificial
<220> FEATURE:
<223> OTHER INFORMATION: Primer

<400> SEQUENCE: 89
catatggaga tgttaatatg tgggtc                                    26

<210> SEQ ID NO 90
<211> LENGTH: 25
<212> TYPE: DNA
<213> ORGANISM: Artificial
<220> FEATURE:
<223> OTHER INFORMATION: Primer

<400> SEQUENCE: 90
caaggttgca gcatgacagc catcg                                     25

<210> SEQ ID NO 91
<211> LENGTH: 20
<212> TYPE: DNA
<213> ORGANISM: Artificial
<220> FEATURE:
<223> OTHER INFORMATION: Primer

<400> SEQUENCE: 91
ggaccgatgg ctgtgtagaa                                           20

<210> SEQ ID NO 92
<211> LENGTH: 20
<212> TYPE: DNA
<213> ORGANISM: Artificial
<220> FEATURE:
<223> OTHER INFORMATION: Primer

<400> SEQUENCE: 92
acggcctcca gaagaagatg                                           20
```